United States Patent [19]
Fritz et al.

[11] Patent Number: 5,922,856
[45] Date of Patent: Jul. 13, 1999

[54] HUMAN PROTEIN CRITICAL FOR HIV REPLICATION

[75] Inventors: Christian C. Fritz, Shrewsbury; Michael R. Green, Boylston, both of Mass.

[73] Assignee: University of Massachusetts, Boston, Mass.

[21] Appl. No.: 08/687,702

[22] Filed: Jun. 27, 1996

Related U.S. Application Data

[60] Provisional application No. 60/000,551, Jun. 27, 1995.

[51] Int. Cl.$^6$ .............................. C07H 21/04; C07K 1/00; C12Q 1/70; A61K 39/00
[52] U.S. Cl. ...................... 536/23.72; 530/350; 530/326; 530/325; 530/324; 435/5; 435/69.1; 424/185.1; 424/208.1
[58] Field of Search ........................... 530/350, 324–326; 435/69.1, 5; 424/208.1, 185.1; 536/23.72

[56] References Cited

PUBLICATIONS

Bogerd et al., "Identification of a Novel Cellular Cofactor for the Rev/Rex Class of Retroviral Regulatory Proteins", Cell 82:485–494, (1995).
Fankhauser et al., "Specific Complex of Human Immunodeficiency Virus Type 1 Rev and Nucleolar B23 Proteins: Dissociation by the Rev Response Element", Molecular and Cellular Biology, 11:2567–2575 (1991).
Fritz et al., "A human nuceioporin–like protein that specifically Interacts with HIV Rev", Letters to Nature, 376:530–533 (1995).
Katahira et al., "Effects of Translation Initiation Factor . . . Deficient in RNA Binding", Journal of Virology, 69:3125–3133 (1995).
Luo et al., "Cellular Protein Modulates Effects of . . . Type 1 Rev", Journal of Virology, 68:3850–3856 (1994).
Malim, et al., "Functional Dissection of the HIV–1 . . . Repressor of Rev Function", Cell 58:205–214, (1989).
Olsen et al., "Interaction of the human . . . stretch of amino acids", Genes & Development, 4:1357–1364 (1990).
Ruhl et al., "Eukaryotic Initiation . . . Domain Mediating Trans–Activation", Journal of Cell Biology, 123:1309–1320 (1993).
Stutz et al., "Identification of a Novel Nuclear . . . HIV–1 Rev Protein in Yeast", Cell, 82:495–506, (1995).
Wen et al., "Identification of a Signal . . . from the Nucleus", Cell, 82:463–473, (1995).
Fabre et al., "Nup 145p is required for nuclear export of mRNA and binds homopolymeric RNA in vitro via a novel conserved motif" Cell 78:275–289, 1994.
Punt et al., "A twin–reporter vector for simultaneous analysis of expression signals of divergently transcribed contiguous genes . . . " Gene 104:119–122, 1991.
Larimer et al., "The REV1 gene of saccharomyces cerevisiae: Isolation, Sequence, and Functional Analysis" J. of Bacteriology 171:230–237, 1989.
J.L. Fox, "No winners against AIDS" Bio/Technology 12:128, 1994.
J.L. Fahey, "Status of immune–based therapies in HIV infection and AIDS" Clin. Exp. Immunol. 88:1–5, 1992.

*Primary Examiner*—Laurie Scheiner
*Assistant Examiner*—Hankyel T. Park
*Attorney, Agent, or Firm*—Fish & Richardson P.C.

[57] ABSTRACT

The present invention provides a human cellular polypeptide, termed hRIP, that is necessary for HIV replication. The polypeptide has a molecular mass of about 59 kDa, having the sequence set forth in FIG. 2a (SEQ ID NO:1). hRIP is the cellular cofactor required to mediate the Rev response. hRIP binds HIV Rev protein and is essential for Rev activity. The invention also includes nucleic acid sequences encoding hRIP, as well as DNA vectors and transformed cells suitable for recombinant expression of this polypeptide.

14 Claims, 10 Drawing Sheets

|  | aa 70 | | | | | | | | | | | | | | | | | | | | | | | 92 | Rev Function gtat | p24 (% of wt) | binding to hRIP in yeast | |
|---|---|---|---|---|---|---|---|---|---|---|---|---|---|---|---|---|---|---|---|---|---|---|---|---|---|---|---|---|
| wt REV: | P | V | P | L | Q | L | P | P | L | E | R | L | T | L | D | C | N | E | D | C | G | T | S | ++ | 100 | ++ | (SEQ ID NO: 3) |
| M 10: | - | - | - | - | - | - | - | - | D | L | - | - | - | - | - | - | - | - | - | - | - | - | - | - | <1 | - | (SEQ ID NO: 4) |
| M 20: | - | - | - | - | - | - | - | - | D | L | - | - | - | - | - | - | - | - | - | - | - | - | - | ++ | 50 | + | (SEQ ID NO: 5) |
| M 22: | - | - | - | - | - | - | - | - | - | - | - | D | L | - | - | - | - | - | - | - | - | - | - | - | <1 | - | (SEQ ID NO: 6) |
| M 25: | - | - | - | - | - | - | - | - | - | - | - | - | - | - | - | - | - | - | E | L | D | - | - | ++ | 70 | ++ | (SEQ ID NO: 7) |
| M 27: | - | - | - | - | - | - | - | A | - | - | - | - | - | - | - | - | - | - | - | - | - | - | - | - | <1 | - | (SEQ ID NO: 8) |
| M 29: | - | - | - | - | - | - | - | - | - | - | - | A | - | - | - | - | - | - | - | - | - | - | - | - | <1 | - | (SEQ ID NO: 9) |
| M 36: | - | - | - | - | - | - | - | - | - | V | - | - | - | - | - | - | - | - | - | - | - | - | - | + | 15 | +/- | (SEQ ID NO: 10) |
| HTLVI Rex: | M | D | A | L | S | A | Q | L | Y | S | S | L | S | L | D | S | P | P | S | P | P | | | | | +++ | (SEQ ID NO: 11) |

FIG. 1

|  | aa 70 | | | | | | | | | | | | | | | | | | | | 92 | Rev Function | | binding to hRIP in yeast | |
|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  | gtat | p24 (% of wt) |  |  |
| wt REV: | P | V | P | L | Q | L | P | P | L | E | R | L | T | L | D | C | N | E | D | C | G | T | S | ++ | 100 | ++ | (SEQ ID NO: 3) |
| M 10: | - | - | - | - | - | - | - | - | - | D | L | - | - | - | - | - | - | - | - | - | - | - | - | - | <1 | - | (SEQ ID NO: 4) |
| M 20: | - | - | - | - | - | - | - | - | - | D | L | - | - | - | - | - | - | - | - | - | - | - | - | ++ | 50 | + | (SEQ ID NO: 5) |
| M 22: | - | - | - | - | - | - | - | - | - | - | - | - | D | L | - | - | - | - | - | - | - | - | - | - | <1 | - | (SEQ ID NO: 6) |
| M 25: | - | - | - | - | - | - | - | - | - | - | - | - | - | - | - | R | L | D | - | - | - | - | - | ++ | 70 | ++ | (SEQ ID NO: 7) |
| M 27: | - | - | - | - | - | - | - | - | - | - | A | - | - | - | - | - | - | - | - | - | - | - | - | - | <1 | - | (SEQ ID NO: 8) |
| M 29: | - | - | - | - | - | - | - | - | - | - | - | - | - | A | - | - | - | - | - | - | - | - | - | - | <1 | - | (SEQ ID NO: 9) |
| M 36: | - | - | - | - | - | - | - | - | - | - | - | V | - | - | - | - | - | - | - | - | - | - | - | + | 15 | +/- | (SEQ ID NO: 10) |

HTLVI Rex: M D A L S A Q L Y S S L S L D S P P S P P            +++   (SEQ ID NO: 11)

```
   1 GCGGGCCCCCGGCGCAGCGCTGCCCGGCTCCCGGCCCTGCCGGCCTCCTCCCTTGGCGCCGCGGCCATGGCGGCCAGCGCGAAG    84
                                                                    M  A  A  S  A  K     6

85 CGGAAGCAGGAGGAGAAGCACCTGAAGATGCTGCGGGACATGACCGGCCTCCCGCACAACCGAAAGTGCTTCGACTGCGACCAG   168
   7  R  K  Q  E  E  K  H  L  K  M  L  R  D  M  T  G  L  P  H  N  R  K [C] F  D [C] D  Q   34

169 CGCGGCCCCACCTACGTTAACATGACCGGTCGGCTCCTTCGTGTGTACCTCCTCCTCCGGCAGCCTGCCGAGGATTAAATCCACCA  252
  35  R  G  P  T  Y  V  N  M  T  V  G  S  F  V [C] T  S [C] S  G  S  L  R  G  L  N  P  P   62

253 CACAGGGTGAAATCTATCTCCATGACAACATTCACACAACAGGAAATTGAATTCTTACAAAAACATGGAAATGAAGTCTGTAAA   336
  63  H  R  V  K  S  I  S  M  T  T  F  T  Q  Q  E  I  E  F  L  Q  K  H  G  N  E  V  C  K   90

337 CAGATTTGGCTAGGATTATTTGATGATAGATCTTCAGCAATTCCAGACTTCAGGGATCCACAAAAAGTGAAAGAGTTTCTACAA   420
  91  Q  I  W  L  G  L  F  D  D  R  S  S  A  I  P  D  F  R  D  P  Q  K  V  K  E  F  L  Q   118

421 GAAAAGTATGAAAAGAAAAGATGGTATGTCCCGCCAGAACAAGCCAAAGTCGTGGCATCAGTTCATGCATCTATTTCAGGGTCC   504
 119  E  K  Y  E  K  K  R  W  Y  V  P  P  E  Q  A  K  V  V  A  S  V  H  A  S  I  S  G  S   146

505 TCTGCCAGTAGCACAAGCAGCACACCTGAGGTCAAACCACTGAAATCTCTTTTAGGGGATTCTGCACCAACACTGCACTTAAAT   588
 147  S  A  S  S  T  S  S  T  P  E  V  K  P  L  K  S  L  L  G  D  S  A  P  T  L  H  L  N   174

589 AAGGGCACACCTAGTCAGTCCCCAGTTGTAGGTCGTTCTCAAGGGCAGCAGCAGGAGAAGAAGCAATTTGACCTTTTAAGTGAT   672
 175  K  G  T  P  S  Q  S  P  V  V  G  R  S  Q  G  Q  Q  Q  E  K  K  Q  F  D  L  L  S  D   202

673 CTCGGCTCAGACATCTTTGCTGCTCCAGCTCCTCAGTCAACAGCTACAGCCAATTTTGCTAACTTTGCACATTTCAACAGTCAT   756
 203  L  G  S  D  I  F  A  A  P  A  P  Q  S  T  A  T  A  N  F  A  N  F  A  H  F  N  S  H   230

757 GCAGCTCAGAATTCTGCAAATGCAGATTTTGCAAACTTTGATGCATTTGGACAGTCTAGTGGTTCGAGTAATTTTGGAGGTTTC   840
 231  A  A  Q  N  S  A  N  A  D  F  A  N  F  D  A [F  G] Q  S  S  G  S  S  N [F  G] G  F   258

841 CCCACAGCAAGTCACTCTCCTTTTCAGCCCCAAACTACAGGTGGAAGTGCTGCATCAGTAAATGCTAATTTTGCTCATTTTGAT   924
 259  P  T  A  S  H  S  P  F  Q  P  Q  T  T  G  G  S  A  A  S  V  N  A  N [F  A  H  F  D]  286

925 AACTTCCCCAAATCCTCCAGTGCTGATTTTGGAACCTTCAATACTTCCCAGAGTCATCAAACAGCATCAGCTGTTAGTAAAGTT  1008
 287  N  F  P  K  S  S  A  D [F  G] T  F  N  T  S  Q  S  H  Q  T  A  S  A  V  S  K  V      314

1009 TCAACGAACAAAGCTGGTTTACAGACTGCAGACAAATATGCAGCACTTGCTAATTTAGACAATATCTTCAGTGCCGGGCAAGGT  1092
 315  S  T  N  K  A  G  L  Q  T  A  D  K  Y  A  A  L  A  N  L  D  N  I  F  S  A  G  Q  G   342

1093 GGTGATCAGGGAAGTGGCTTTGGGACCACAGGTAAAGCTCCTGTTGGTTCTGTGGTTTCAGTTCCCAGTCAGTCAAGTGCATCT  1176
 343  G  D  Q  G  S  G [F  G] T  T  G  K  A  P  V  G  S  V  V  S  V  P  S  Q  S  S  A  S   370

1177 TCAGACAAGTATGCAGCTCTGGCAGAACTAGACAGCGTTTTCAGTTCTGCAGCGCACCTCCAGTAATGCGTATACTTCCACAGT  1260
 371  S  D  K  Y  A  A  L  A  E  L  D  S  V  F  S  S  A  A  T  S  S  N  A  Y  T  S  T  S   398

1261 AATGCTAGCAGCAATGTTTTTGGAACAGTGCCAGTGGTTGCTTCTGCACAGACACAGCCTGCTTCATCAAGTGTGCCTGCTCCA  1344
 399  N  A  S  S  N  V [F  G] T  V  P  V  V  A  S  A  Q  T  Q  P  A  S  S  V  P  A  P      426

1345 TTTGGACGTACGCCTTCCACAAATCCATTTGTTGCTGCTGCTGGTCCTTCTGTGGCATCTTCTACAAACCCATTTCAGACCAAT  1428
 427 [F  G] R  T  P  S  T  N  P  F  V  A  A  A  G  P  S  V  A  S  S  T  N  P  F  Q  T  N   454

1429 GCCAGAGGAGCAACAGCGGCAAACCTTTGGCACTGCATCCATGAGCATGCCCACGGGATTCGGCACTCCTGCTCCCTACAGTCTT  1512
 455  A  R  G  A  T  A  A  T [F  G] T  A  S  H  S  M  P  T  G [F  G] T  P  A  P  Y  S  L   482

1513 CCCACCAGCTTTAGTGGCAGCTTTCAGCAGCCTGCCTTTCCAGCCCAAGCAGCTTTCCCTCAACAGACAGCTTTTCTCAACAG   1596
 483  P  T  S  F  S  G  S  F  Q  Q  P  A  F  P  A  Q  A  A  F  P  Q  Q  T  A  F  S  Q  Q   510

1597 CCCAATGGTGCAGGTTTTGCAGCATTTGGACAAACAAAGCCAGTAGTAACCCCTTTTGGTCAAGTTGCAGCTGCTGGAGTATCT  1680
 511  P  N  G  A  G  F  A  A [F  G] Q  T  K  P  V  V  T  P [F  G] Q  V  A  A  A  G  V  S   538

1681 AGTAATCCTTTTATGACTGGTGCACCAACAGGACAATTTCCAACAGGAAGCTCATCAACCAATCCTTTCTTATAGCCTTATATA  1764
 539  S  N  P  F  M  T  G  A  P  T  G  Q  F  P  T  G  S  S  T  N  P  F  L  *               566
                                                                        . (SEQ ID NO: 1)
1765 GACAATTTACTGGAACGAACTTTTATGTGGTCACATTACATCTCTCCACCTCTTGCACTGTTGTCTTGTTCACTGATCTTAGC  1848
1849 TTTAAACACAAGAGAAGTCTTTAAAAAGCCTGCATTGTGTATTAAACACCAGGTAATATGTGCAAAACCAGGGCTCCAGTAAC  1932
1933 ACCTTCTAACCTGTGAATTGGCAGAAAAGGGTAGCCGTATCATGTATATTAAAATTGGCTAATATTAAGTTATTGCAGATACCA  2016
2017 CATTCATTATGCTGCAGTACTGTACATATTTTTCTTAGAAATTAGCTATTTGTGCATATCAGTATTTGTAACTTTAACACATTG  2100
2101 TTATGTGAGAAATGTTACTGGGGAAATAGATCAGCCATTTTAAGGTGCTGTCATATATCTTGAATGAATGACCTAAAATCAT    2184
2185 TTTAACCATTGCTACTGGAAAGTAACAGAGTCAAAATTGGAAGGTTTTATTCATTCTTGAATTTTTCCTTTCTAAAGAGCTCTT  2268
2269 CTATTTATACATGCCTAAATTCTTTTAAAATGTAGAGGGATACCCTGTCTGCATAATAAAGCTGATCATGTTTTGCTACAGTTTG  2352
2353 CAGGTGAAAAAAAATAAATATTATAAAATAAAAAAAAAAAAAAAAAGAAAAAAAA  2406      (SEQ ID NO: 2)
```

245 D A F G   (SEQ ID NO:20)
254 S N F G   (SEQ ID NO:21)
294 A D F G   (SEQ ID NO:22)
347 S G F G   (SEQ ID NO:23)
403 N V F G   (SEQ ID NO:24)
425 A P F G   (SEQ ID NO:25)
461 A T F G   (SEQ ID NO:26)
472 T G F G   (SEQ ID NO:27)
517 A A F G   (SEQ ID NO:28)
527 T P F G   (SEQ ID NO:29)

221 F A N F A H F   (SEQ ID NO:30)
241 F A N F D A F   (SEQ ID NO:31)
282 F A H F D N F   (SEQ ID NO:32)

325 D K Y A A L A N L D N I F S   (SEQ ID NO:33)
372 D K Y A A L A E L D S V F S   (SEQ ID NO:34)

432 S T N P F   (SEQ ID NO:35)
446 S T N P F   (SEQ ID NO:35)
538 S T N P F   (SEQ ID NO:35)
557 S T N P F   (SEQ ID NO:35)

FIG. 2e

```
hRIP    ATANFANFAHFNSHAAQNSANADFANFDAFGQSSGGSSNFGGFPTASHSPFQPQTTGGSAA
        :::  ::|:::|||:::  :::      :::|||:::|:::  |::  : ::|
NUP214  SSSGFSS-PAEGTTAPGVFGQTTEGQASVEGQSASSAA-SVEFSF-SQPGFSSVPAFGQPA hRIP    SVNANFAHFDNF-PKSSSADFGTFNTSQSHQTASAVSKVSTNKAGLQTADKYAALANLDN
        |  ::|||:::|  :::   ::  |:  :::::   :::      :::  ::: :::
NUP214  SSTPTSTSGSVEGAASSTSSSSSEFGQSSPNTGGLFGQSNAPAFGQSPGFGQGGSVFG hRIP    IFSAGQGGDQGSGFG-----TTGKAPVGSVVSVPSQSSASSDKYAALAELDSVFSSAATS
        | |  ::: ::|||::    :|:||:    :::              :::|:::::|
NUP214  GTSAATTAATSGEFSFCQASGFGSSNTGSVFGQAASTGGIVFGQQSSSSSGSVEGSGNTG hRIP    SNA---YTSTNASSNVFGTVPVVASAQ---TQPASSSVPAFGRTPSTNPFVAAAGPSVA
        :::   ::: :::  :||  ::       :||   :|||:||  ||:||:|  ::|||
NUP214  RGGGFFSGLGGKPSQDAANKNPFSSASGGFGSTATSNTSNLFG-NSGAKTEGGFASSSFG hRIP    ---SSTNEFQTNARGATAAIFGTASMSMPTGFGTPAPYSLPTSFSGSFQQPAFPAQAAFPQ
        :::     ||: :::::| ||:|::  :||||||:| :  : || ::  |:  |::||
NUP214  EQKPTGTESSGGGSVASQGEFSSPNKTGGEFGSSVASSGSAAPVFGSPPTEGGSPGFVPAEGS hRIP    QTAFSQQPNGAGFEAAFGQTKPVVTP--FGQVAAAGVSSNPFMTGAPTGQFPTGSSSTNFFL (SEQ ID NO:36)
        ::::|||:  :||||:||   ::|   ||: ::::|:::|:||:|:|| |||: :::::|
NUP214  APAFTSPLGSTGGKVEGETAAASAGEGFGSSNTTSFGTLASQNAPTEGSLSQQTSGFG    (SEQ ID NO:37)
```

FIG. 2f

α hRIP

Mab 322

α hRIP nuclear periphery nuclear surface

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 562 amino acids
      (B) TYPE: amino acid
      (D) TOPOLOGY: linear (ii) MOLECULE TYPE: protein (v) FRAGMENT TYPE: internal (xi) SEQUENCE DESCRIPTION: SEQ ID NO:1:

```
Met Ala Ala Ser Ala Lys Arg Lys Gln Glu Glu Lys His Leu Lys Met
  1               5                  10                  15

Leu Arg Asp Met Thr Gly Leu Pro His Asn Arg Lys Cys Phe Asp Cys
                 20                  25                  30

Asp Gln Arg Gly Pro Thr Tyr Val Asn Met Thr Val Gly Ser Phe Val
             35                  40                  45

Cys Thr Ser Cys Ser Gly Ser Leu Arg Gly Leu Asn Pro Pro His Arg
         50                  55                  60

Val Lys Ser Ile Ser Met Thr Thr Phe Thr Gln Gln Glu Ile Glu Phe
 65                  70                  75                  80

Leu Gln Lys His Gly Asn Glu Val Cys Lys Gln Ile Trp Leu Gly Leu
                 85                  90                  95

Phe Asp Asp Arg Ser Ser Ala Ile Pro Asp Phe Arg Asp Pro Gln Lys
                100                 105                 110

Val Lys Glu Phe Leu Gln Glu Lys Tyr Glu Lys Lys Arg Trp Tyr Val
            115                 120                 125

Pro Pro Glu Gln Ala Lys Val Val Ala Ser Val His Ala Ser Ile Ser
        130                 135                 140

Gly Ser Ser Ala Ser Ser Thr Ser Ser Thr Pro Glu Val Lys Pro Leu
145                 150                 155                 160
```

```
Lys Ser Leu Leu Gly Asp Ser Ala Pro Thr Leu His Leu Asn Lys Gly
                165                 170                 175

Thr Pro Ser Gln Ser Pro Val Val Gly Arg Ser Gln Gly Gln Gln Gln
            180                 185                 190

Glu Lys Lys Gln Phe Asp Leu Leu Ser Asp Leu Gly Ser Asp Ile Phe
        195                 200                 205

Ala Ala Pro Ala Pro Gln Ser Thr Ala Thr Ala Asn Phe Ala Asn Phe
    210                 215                 220

Ala His Phe Asn Ser His Ala Ala Gln Asn Ser Ala Asn Ala Asp Phe
225                 230                 235                 240

Ala Asn Phe Asp Ala Phe Gly Gln Ser Ser Gly Ser Ser Asn Phe Gly
                245                 250                 255

Gly Phe Pro Thr Ala Ser His Ser Pro Phe Gln Pro Gln Thr Thr Gly
            260                 265                 270

Gly Ser Ala Ala Ser Val Asn Ala Asn Phe Ala His Phe Asp Asn Phe
        275                 280                 285

Pro Lys Ser Ser Ser Ala Asp Phe Gly Thr Phe Asn Thr Ser Gln Ser
    290                 295                 300

His Gln Thr Ala Ser Ala Val Ser Lys Val Ser Thr Asn Lys Ala Gly
305                 310                 315                 320

Leu Gln Thr Ala Asp Lys Tyr Ala Ala Leu Ala Asn Leu Asp Asn Ile
                325                 330                 335

Phe Ser Ala Gly Gln Gly Gly Asp Gln Gly Ser Gly Phe Gly Thr Thr
            340                 345                 350

Gly Lys Ala Pro Val Gly Ser Val Val Ser Val Pro Ser Gln Ser Ser
        355                 360                 365

Ala Ser Ser Asp Lys Tyr Ala Ala Leu Ala Glu Leu Asp Ser Val Phe
    370                 375                 380

Ser Ser Ala Ala Thr Ser Ser Asn Ala Tyr Thr Ser Thr Ser Asn Ala
385                 390                 395                 400

Ser Ser Asn Val Phe Gly Thr Val Pro Val Val Ala Ser Ala Gln Thr
                405                 410                 415

Gln Pro Ala Ser Ser Val Pro Ala Pro Phe Gly Arg Thr Pro Ser
            420                 425                 430

Thr Asn Pro Phe Val Ala Ala Gly Pro Ser Val Ala Ser Ser Thr
        435                 440                 445

Asn Pro Phe Gln Thr Asn Ala Arg Gly Ala Thr Ala Ala Thr Phe Gly
    450                 455                 460

Thr Ala Ser Met Ser Met Pro Thr Gly Phe Gly Thr Pro Ala Pro Tyr
465                 470                 475                 480

Ser Leu Pro Thr Ser Phe Ser Gly Ser Phe Gln Gln Pro Ala Phe Pro
                485                 490                 495

Ala Gln Ala Ala Phe Pro Gln Thr Ala Phe Ser Gln Gln Pro Asn
            500                 505                 510

Gly Ala Gly Phe Ala Ala Phe Gly Gln Thr Lys Pro Val Val Thr Pro
        515                 520                 525

Phe Gly Gln Val Ala Ala Ala Gly Val Ser Ser Asn Pro Phe Met Thr
    530                 535                 540

Gly Ala Pro Thr Gly Gln Phe Pro Thr Gly Ser Ser Thr Asn Pro
545                 550                 555                 560

Phe Leu (2) INFORMATION FOR SEQ ID NO:2:
```

(i) SEQUENCE CHARACTERISTICS:
    (A) LENGTH: 2406 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: Coding Sequence
    (B) LOCATION: 67...1752

(xi) SEQUENCE DESCRIPTION: SEQ ID NO:2:

```
GCGGGCCCCC GGCGCAGCGC TGCCCGGCTC CCGGCCCTGC CGGCCTCCTC CGTTGGCGCC      60

GCGGCC ATG GCG GCC AGC GCG AAG CGG AAG CAG GAG GAG AAG CAC CTG        108
       Met Ala Ala Ser Ala Lys Arg Lys Gln Glu Glu Lys His Leu
         1               5                  10

AAG ATG CTG CGG GAC ATG ACC GGC CTC CCG CAC AAC CGA AAG TGC TTC       156
Lys Met Leu Arg Asp Met Thr Gly Leu Pro His Asn Arg Lys Cys Phe
 15              20                  25                  30

GAC TGC GAC CAG CGC GGC CCC ACC TAC GTT AAC ATG ACG GTC GGC TCC       204
Asp Cys Asp Gln Arg Gly Pro Thr Tyr Val Asn Met Thr Val Gly Ser
                 35                  40                  45

TTC GTG TGT ACC TCC TGC TCC GGC AGC CTG CGA GGA TTA AAT CCA CCA       252
Phe Val Cys Thr Ser Cys Ser Gly Ser Leu Arg Gly Leu Asn Pro Pro
             50                  55                  60

CAC AGG GTG AAA TCT ATC TCC ATG ACA ACA TTC ACA CAA CAG GAA ATT       300
His Arg Val Lys Ser Ile Ser Met Thr Thr Phe Thr Gln Gln Glu Ile
         65                  70                  75

GAA TTC TTA CAA AAA CAT GGA AAT GAA GTC TGT AAA CAG ATT TGG CTA       348
Glu Phe Leu Gln Lys His Gly Asn Glu Val Cys Lys Gln Ile Trp Leu
     80                  85                  90

GGA TTA TTT GAT GAT AGA TCT TCA GCA ATT CCA GAC TTC AGG GAT CCA       396
Gly Leu Phe Asp Asp Arg Ser Ser Ala Ile Pro Asp Phe Arg Asp Pro
 95                 100                 105                 110

CAA AAA GTG AAA GAG TTT CTA CAA GAA AAG TAT GAA AAG AAA AGA TGG       444
Gln Lys Val Lys Glu Phe Leu Gln Glu Lys Tyr Glu Lys Lys Arg Trp
                115                 120                 125

TAT GTC CCG CCA GAA CAA GCC AAA GTC GTG GCA TCA GTT CAT GCA TCT       492
Tyr Val Pro Pro Glu Gln Ala Lys Val Val Ala Ser Val His Ala Ser
            130                 135                 140

ATT TCA GGG TCC TCT GCC AGT AGC ACA AGC AGC ACA CCT GAG GTC AAA       540
Ile Ser Gly Ser Ser Ala Ser Ser Thr Ser Ser Thr Pro Glu Val Lys
        145                 150                 155

CCA CTG AAA TCT CTT TTA GGG GAT TCT GCA CCA ACA CTG CAC TTA AAT       588
Pro Leu Lys Ser Leu Leu Gly Asp Ser Ala Pro Thr Leu His Leu Asn
    160                 165                 170

AAG GGC ACA CCT AGT CAG TCC CCA GTT GTA GGT CGT TCT CAA GGG CAG       636
Lys Gly Thr Pro Ser Gln Ser Pro Val Val Gly Arg Ser Gln Gly Gln
175                 180                 185                 190

CAG CAG GAG AAG AAG CAA TTT GAC CTT TTA AGT GAT CTC GGC TCA GAC       684
Gln Gln Glu Lys Lys Gln Phe Asp Leu Leu Ser Asp Leu Gly Ser Asp
                195                 200                 205

ATC TTT GCT GCT CCA GCT CCT CAG TCA ACA GCT ACA GCC AAT TTT GCT       732
Ile Phe Ala Ala Pro Ala Pro Gln Ser Thr Ala Thr Ala Asn Phe Ala
            210                 215                 220

AAC TTT GCA CAT TTC AAC AGT CAT GCA GCT CAG AAT TCT GCA AAT GCA       780
Asn Phe Ala His Phe Asn Ser His Ala Ala Gln Asn Ser Ala Asn Ala
        225                 230                 235

GAT TTT GCA AAC TTT GAT GCA TTT GGA CAG TCT AGT GGT TCG AGT AAT       828
Asp Phe Ala Asn Phe Asp Ala Phe Gly Gln Ser Ser Gly Ser Ser Asn
    240                 245                 250
```

-continued

| | |
|---|---|
| TTT GGA GGT TTC CCC ACA GCA AGT CAC TCT CCT TTT CAG CCC CAA ACT<br>Phe Gly Gly Phe Pro Thr Ala Ser His Ser Pro Phe Gln Pro Gln Thr<br>255                              260                           265                           270 | 876 |
| ACA GGT GGA AGT GCT GCA TCA GTA AAT GCT AAT TTT GCT CAT TTT GAT<br>Thr Gly Gly Ser Ala Ala Ser Val Asn Ala Asn Phe Ala His Phe Asp<br>                           275                           280                           285 | 924 |
| AAC TTC CCC AAA TCC TCC AGT GCT GAT TTT GGA ACC TTC AAT ACT TCC<br>Asn Phe Pro Lys Ser Ser Ser Ala Asp Phe Gly Thr Phe Asn Thr Ser<br>             290                           295                           300 | 972 |
| CAG AGT CAT CAA ACA GCA TCA GCT GTT AGT AAA GTT TCA ACG AAC AAA<br>Gln Ser His Gln Thr Ala Ser Ala Val Ser Lys Val Ser Thr Asn Lys<br>                 305                           310                           315 | 1020 |
| GCT GGT TTA CAG ACT GCA GAC AAA TAT GCA GCA CTT GCT AAT TTA GAC<br>Ala Gly Leu Gln Thr Ala Asp Lys Tyr Ala Ala Leu Ala Asn Leu Asp<br>320                              325                           330 | 1068 |
| AAT ATC TTC AGT GCC GGG CAA GGT GGT GAT CAG GGA AGT GGC TTT GGG<br>Asn Ile Phe Ser Ala Gly Gln Gly Gly Asp Gln Gly Ser Gly Phe Gly<br>335                              340                           345                           350 | 1116 |
| ACC ACA GGT AAA GCT CCT GTT GGT TCT GTG GTT TCA GTT CCC AGT CAG<br>Thr Thr Gly Lys Ala Pro Val Gly Ser Val Val Ser Val Pro Ser Gln<br>                           355                           360                           365 | 1164 |
| TCA AGT GCA TCT TCA GAC AAG TAT GCA GCT CTG GCA GAA CTA GAC AGC<br>Ser Ser Ala Ser Ser Asp Lys Tyr Ala Ala Leu Ala Glu Leu Asp Ser<br>                 370                           375                           380 | 1212 |
| GTT TTC AGT TCT GCA GCC ACC TCC AGT AAT GCG TAT ACT TCC ACA AGT<br>Val Phe Ser Ser Ala Ala Thr Ser Ser Asn Ala Tyr Thr Ser Thr Ser<br>             385                           390                           395 | 1260 |
| AAT GCT AGC AGC AAT GTT TTT GGA ACA GTG CCA GTG GTG GCT TCT GCA<br>Asn Ala Ser Ser Asn Val Phe Gly Thr Val Pro Val Val Ala Ser Ala<br>400                              405                           410 | 1308 |
| CAG ACA CAG CCT GCT TCA TCA AGT GTG CCT GCT CCA TTT GGA CGT ACG<br>Gln Thr Gln Pro Ala Ser Ser Ser Val Pro Ala Pro Phe Gly Arg Thr<br>415                              420                           425                           430 | 1356 |
| CCT TCC ACA AAT CCA TTT GTT GCT GCT GCT GGT CCT TCT GTG GCA TCT<br>Pro Ser Thr Asn Pro Phe Val Ala Ala Ala Gly Pro Ser Val Ala Ser<br>                           435                           440                           445 | 1404 |
| TCT ACA AAC CCA TTT CAG ACC AAT GCC AGA GGA GCA ACA GCG GCA ACC<br>Ser Thr Asn Pro Phe Gln Thr Asn Ala Arg Gly Ala Thr Ala Ala Thr<br>                 450                           455                           460 | 1452 |
| TTT GGC ACT GCA TCC ATG AGC ATG CCC ACG GGA TTC GGC ACT CCT GCT<br>Phe Gly Thr Ala Ser Met Ser Met Pro Thr Gly Phe Gly Thr Pro Ala<br>                           465                           470                           475 | 1500 |
| CCC TAC AGT CTT CCC ACC AGC TTT AGT GGC AGC TTT CAG CAG CCT GCC<br>Pro Tyr Ser Leu Pro Thr Ser Phe Ser Gly Ser Phe Gln Gln Pro Ala<br>480                              485                           490 | 1548 |
| TTT CCA GCC CAA GCA GCT TTC CCT CAA CAG ACA GCT TTT TCT CAA CAG<br>Phe Pro Ala Gln Ala Ala Phe Pro Gln Gln Thr Ala Phe Ser Gln Gln<br>495                              500                           505                           510 | 1596 |
| CCC AAT GGT GCA GGT TTT GCA GCA TTT GGA CAA ACA AAG CCA GTA GTA<br>Pro Asn Gly Ala Gly Phe Ala Ala Phe Gly Gln Thr Lys Pro Val Val<br>                           515                           520                           525 | 1644 |
| ACC CCT TTT GGT CAA GTT GCA GCT GCT GGA GTA TCT AGT AAT CCT TTT<br>Thr Pro Phe Gly Gln Val Ala Ala Ala Gly Val Ser Ser Asn Pro Phe<br>                           530                           535                           540 | 1692 |
| ATG ACT GGT GCA CCA ACA GGA CAA TTT CCA ACA GGA AGC TCA TCA ACC<br>Met Thr Gly Ala Pro Thr Gly Gln Phe Pro Thr Gly Ser Ser Ser Thr<br>545                              550                           555 | 1740 |
| AAT CCT TTC TTA TAGCCTTATA TAGACAATTT ACTGGAACGA ACTTTTATGT GGTCA<br>Asn Pro Phe Leu<br>             560 | 1797 |

```
CATTACATCT CTCCACCTCT TGCACTGTTG TCTTGTTTCA CTGATCTTAG CTTTAAACAC    1857

AAGAGAAGTC TTTAAAAAGC CTGCATTGTG TATTAAACAC CAGGTAATAT GTGCAAAACC    1917

GAGGGCTCCA GTAACACCTT CTAACCTGTG AATTGGCAGA AAAGGGTAGC GGTATCATGT    1977

ATATTAAAAT TGGCTAATAT TAAGTTATTG CAGATACCAC ATTCATTATG CTGCAGTACT    2037

GTACATATTT TTCTTAGAAA TTAGCTATTT GTGCATATCA GTATTTGTAA CTTTAACACA    2097

TTGTTATGTG AGAAATGTTA CTGGGGAAAT AGATCAGCCA CTTTTAAGGT GCTGTCATAT    2157

ATCTTGGAAT GAATGACCTA AAATCATTTT AACCATTGCT ACTGAAAGT AACAGAGTCA     2217

AAATTGGAAG GTTTTATTCA TTCTTGAATT TTTCCTTTCT AAAGAGCTCT TCTATTTATA    2277

CATGCCTAAA TTCTTTTAAA ATGTAGAGGG ATACCTGTCG GCATAATAAA GCTGATCATG    2337

TTTTGCTACA GTTTGCAGGT GAAAAAAAAT AAATATTATA AAATAAAAAA AAAAAAAAA    2397

AAAAAAAAA                                                          2406
```

(2) INFORMATION FOR SEQ ID NO:3:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:3:

```
Pro Val Pro Leu Gln Leu Pro Pro Leu Glu Arg Leu Thr Leu Asp Cys
1               5                   10                  15

Asn Glu Glu Leu Asp Thr Ser
            20
```

(2) INFORMATION FOR SEQ ID NO:4:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:4:

```
Pro Val Pro Leu Gln Leu Pro Pro Asp Leu Arg Leu Thr Leu Asp Cys
1               5                   10                  15

Asn Glu Asp Cys Gly Thr Ser
            20
```

(2) INFORMATION FOR SEQ ID NO:5:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:5:

```
Pro Val Pro Leu Gln Leu Pro Pro Leu Asp Leu Thr Leu Asp Cys
1               5                   10                  15
```

Asn Glu Asp Cys Gly Thr Ser
        20

(2) INFORMATION FOR SEQ ID NO:6:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:6:

Pro Val Pro Leu Gln Leu Pro Pro Leu Glu Arg Leu Thr Asp Leu Cys
1               5                   10                  15

Asn Glu Asp Cys Gly Thr Ser
        20

(2) INFORMATION FOR SEQ ID NO:7:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:7:

Pro Val Pro Leu Gln Leu Pro Pro Leu Glu Arg Leu Thr Leu Asp Cys
1               5                   10                  15

Asn Glu Glu Leu Asp Thr Ser
        20

(2) INFORMATION FOR SEQ ID NO:8:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:8:

Pro Val Pro Leu Gln Leu Pro Pro Ala Glu Arg Leu Thr Leu Asp Cys
1               5                   10                  15

Asn Glu Asp Cys Gly Thr Ser
        20

(2) INFORMATION FOR SEQ ID NO:9:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO:9:

Pro Val Pro Leu Gln Leu Pro Pro Leu Glu Arg Leu Thr Ala Asp Cys
1               5                   10                  15

Asn Glu Asp Cys Gly Thr Ser
        20

(2) INFORMATION FOR SEQ ID NO:10:

(i) SEQUENCE CHARACTERISTICS:

(A) LENGTH: 23 amino acids
          (B) TYPE: amino acid
          (D) TOPOLOGY: linear (ii) MOLECULE TYPE: protein (xi) SEQUENCE DESCRIPTION: SEQ ID NO:10:

Pro Val Pro Leu Gln Leu Pro Pro Leu Val Arg Leu Thr Leu Asp Cys
1               5                   10                  15

Asn Glu Asp Cys Gly Thr Ser
            20

(2) INFORMATION FOR SEQ ID NO:11:

(i) SEQUENCE CHARACTERISTICS:
          (A) LENGTH: 21 amino acids
          (B) TYPE: amino acid
          (D) TOPOLOGY: linear (ii) MOLECULE TYPE: protein (xi) SEQUENCE DESCRIPTION: SEQ ID NO:11:

Met Asp Ala Leu Ser Ala Gln Leu Tyr Ser Ser Leu Ser Leu Asp Ser
1               5                   10                  15

Pro Pro Ser Pro Pro
            20

(2) INFORMATION FOR SEQ ID NO:12:

(i) SEQUENCE CHARACTERISTICS:
          (A) LENGTH: 61 amino acids
          (B) TYPE: amino acid
          (D) TOPOLOGY: linear (ii) MOLECULE TYPE: protein (xi) SEQUENCE DESCRIPTION: SEQ ID NO:12:

Asn Arg Lys Cys Phe Asp Cys Asp Gln Arg Gly Pro Thr Tyr Val Asn
1               5                   10                  15

Met Tyr Val Gly Ser Phe Val Cys Thr Ser Cys Ser Gly Ser Leu Arg
            20                  25                  30

Gly Leu Asn Pro Pro His Arg Val Lys Ser Ile Ser Met Thr Thr Phe
        35                  40                  45

Thr Gln Gln Glu Ile Glu Phe Leu Gln Lys His Gly Asn
50                  55                  60

(2) INFORMATION FOR SEQ ID NO:13:

(i) SEQUENCE CHARACTERISTICS:
          (A) LENGTH: 62 amino acids
          (B) TYPE: amino acid
          (D) TOPOLOGY: linear (ii) MOLECULE TYPE: protein (xi) SEQUENCE DESCRIPTION: SEQ ID NO:13:

Asn Asn Asn Cys Phe Glu Cys Lys Ser Val Asn Pro Gln Phe Val Ser
1               5                   10                  15

Cys Ser Phe Gly Ile Phe Ile Cys Val Asn Cys Ala Asn Leu Leu Arg
            20                  25                  30

Gly Met Gly Thr Asn Ile Phe Cys Val Lys Ser Ile Thr Met Asp Asn
        35                  40                  45

Phe Glu Glu Lys Asp Val Arg Arg Val Glu Lys Ser Gly Asn
50                  55                  60

(2) INFORMATION FOR SEQ ID NO:14:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:14:

```
Asn Lys Met Cys Phe Asp Cys Ser Ala Lys Asn Pro Thr Trp Ala Ser
 1               5                  10                  15

Val Thr Tyr Gly Ile Phe Leu Cys Leu Asp Cys Ser Ala Val His Arg
            20                  25                  30

Ser Leu Gly Val His Ile Thr Phe Val Arg Ser Thr Asn Leu Asp Ser
        35                  40                  45

Trp Thr Pro Asp Gln Leu Lys Met Met Ala Phe Gly Gly Asn
    50                  55                  60
```

(2) INFORMATION FOR SEQ ID NO:15:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:15:

```
Asn Lys Lys Cys Met Asp Cys Gly Ala Pro Asn Pro Gln Trp Ala Thr
 1               5                  10                  15

Pro Lys Phe Gly Ala Phe Ile Cys Leu Glu Cys Ala Gly Thr His Arg
            20                  25                  30

Gly Leu Gly Val His Ile Ser Phe Val Arg Ser Ile Thr Met Asp Gln
        35                  40                  45

Phe Lys Pro Glu Glu Leu Leu Arg Met Glu Lys Gly Gly Asn
    50                  55                  60
```

(2) INFORMATION FOR SEQ ID NO:16:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:16:

```
Asn Lys Tyr Cys Ala Asp Cys Gln Ala Lys Thr Gln Arg Trp Ala Ala
 1               5                  10                  15

Trp Asn Leu Gly Val Phe Ile Cys Ile Arg Cys Ala Gly Ile His Arg
            20                  25                  30

Asn Leu Gly Val His Ile Ser Lys Val Arg Ser Val Glu Leu Asp Ser
        35                  40                  45

Trp Thr Pro Glu Gln Val Gln Thr Met Arg Val Met Gly Asn
    50                  55                  60
```

(2) INFORMATION FOR SEQ ID NO:17:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:17:

Asn Arg Val Cys Ala Asp Cys Gly Ala Pro Asp Pro Lys Trp Ala Ser
1               5                   10                  15

Leu Asn Ile Gly Val Phe Ile Cys Leu Lys Cys Cys Gly Val His Arg
            20                  25                  30

Ser Leu Gly Ser His Ile Ser Lys Val Leu Ser Val Thr Leu Asp Glu
            35                  40                  45

Trp Ser Asp Glu Glu Val Asp Ser Met Ile Glu
50                      55

(2) INFORMATION FOR SEQ ID NO:18:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:18:

Asn Ala Ser Cys Cys Asp Cys Gly Leu Ala Asp Pro Arg Trp Ala Ser
1               5                   10                  15

Ile Asn Leu Gly Leu Thr Leu Cys Ile Glu Cys Ser Gly Ile His Arg
            20                  25                  30

Ser Leu Gly Val His Phe Ser Lys Val Arg Ser Leu Thr Leu Asp Thr
            35                  40                  45

Trp Glu Pro Glu Leu Leu Lys Leu Met Cys Glu Leu Gly Asn
50                  55                  60

(2) INFORMATION FOR SEQ ID NO:19:

(i) SEQUENCE CHARACTERISTICS:
        (A) LENGTH: 62 amino acids
        (B) TYPE: amino acid
        (D) TOPOLOGY: linear (ii) MOLECULE TYPE: protein (xi) SEQUENCE DESCRIPTION: SEQ ID NO:19:

Asn Ala Gln Cys Cys Asp Cys Arg Glu Pro Ala Pro Glu Trp Ala Ser
1               5                   10                  15

Ile Asn Leu Gly Val Thr Leu Cys Ile Gln Cys Ser Gly Ile His Arg
            20                  25                  30

Ser Leu Gly Val His Phe Ser Lys Val Arg Ser Leu Thr Leu Asp Ser
            35                  40                  45

Trp Glu Pro Glu Leu Leu Lys Leu Met Cys Glu Leu Gly Asn
50                  55                  60

(2) INFORMATION FOR SEQ ID NO:20:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:20:

Asp Ala Phe Gly
1

(2) INFORMATION FOR SEQ ID NO:21:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:21:

Ser Asn Phe Gly
1

(2) INFORMATION FOR SEQ ID NO:22:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:22:

Ala Asp Phe Gly
1

(2) INFORMATION FOR SEQ ID NO:23:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:23:

Ser Gly Phe Gly
1

(2) INFORMATION FOR SEQ ID NO:24:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:24:

Asn Val Phe Gly
1

(2) INFORMATION FOR SEQ ID NO:25:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:25:

Ala Pro Phe Gly
1

(2) INFORMATION FOR SEQ ID NO:26:

(i) SEQUENCE CHARACTERISTICS:
        (A) LENGTH: 4 amino acids
        (B) TYPE: amino acid

```
        (D) TOPOLOGY: linear (ii) MOLECULE TYPE: protein (xi) SEQUENCE DESCRIPTION: SEQ ID NO:26:

Ala Thr Phe Gly
1

(2) INFORMATION FOR SEQ ID NO:27:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:27:

Thr Gly Phe Gly
1

(2) INFORMATION FOR SEQ ID NO:28:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:28:

Ala Ala Phe Gly
1

(2) INFORMATION FOR SEQ ID NO:29:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:29:

Thr Pro Phe Gly
1

(2) INFORMATION FOR SEQ ID NO:30:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:30:

Phe Ala Asn Phe Ala His Phe
1               5

(2) INFORMATION FOR SEQ ID NO:31:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:31:
```

```
Phe Ala Asn Phe Asp Ala Phe
 1               5
```

(2) INFORMATION FOR SEQ ID NO:32:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:32:

```
Phe Ala His Phe Asp Asn Phe
 1               5
```

(2) INFORMATION FOR SEQ ID NO:33:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:33:

```
Asp Lys Tyr Ala Ala Leu Ala Asn Leu Asp Asn Ile Phe Ser
 1               5                  10
```

(2) INFORMATION FOR SEQ ID NO:34:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:34:

```
Asp Lys Tyr Ala Ala Leu Ala Glu Leu Asp Ser Val Phe Ser
 1               5                  10
```

(2) INFORMATION FOR SEQ ID NO:35:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:35:

```
Ser Thr Asn Pro Phe
 1               5
```

(2) INFORMATION FOR SEQ ID NO:36:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO:36:

```
Ala Thr Ala Asn Phe Ala Asn Phe Ala His Phe Asn Ser His Ala Ala
 1               5                  10                  15

Gln Asn Ser Ala Asn Ala Asp Phe Ala Asn Phe Asp Ala Phe Gly Gln
```

```
                    20                  25                  30
Ser Ser Gly Ser Ser Asn Phe Gly Gly Phe Pro Thr Ala Ser His Ser
             35                  40                  45
Pro Phe Gln Pro Gln Thr Thr Gly Gly Ser Ala Ala Ser Val Asn Ala
 50                  55                  60
Asn Phe Ala His Phe Asp Asn Phe Pro Lys Ser Ser Ser Ala Asp Phe
 65                  70                  75                  80
Gly Thr Phe Asn Thr Ser Gln Ser His Gln Thr Ala Ser Ala Val Ser
             85                  90                  95
Lys Val Ser Thr Asn Lys Ala Gly Leu Gln Thr Ala Asp Lys Tyr Ala
             100                 105                 110
Ala Leu Ala Asn Leu Asp Asn Ile Phe Ser Ala Gly Gln Gly Gly Asp
             115                 120                 125
Gln Gly Ser Gly Phe Gly Thr Thr Gly Lys Ala Pro Val Gly Ser Val
 130                 135                 140
Val Ser Val Pro Ser Gln Ser Ser Ala Ser Ser Asp Lys Tyr Ala Ala
 145                 150                 155                 160
Leu Ala Glu Leu Asp Ser Val Phe Ser Ser Ala Thr Ser Ser Asn
             165                 170                 175
Ala Tyr Thr Ser Thr Ser Asn Ala Ser Ser Asn Val Phe Gly Thr Val
             180                 185                 190
Pro Val Val Ala Ser Ala Gln Thr Gln Pro Ala Ser Ser Ser Val Pro
             195                 200                 205
Ala Pro Phe Gly Arg Thr Pro Ser Thr Asn Pro Phe Val Ala Ala Ala
 210                 215                 220
Gly Pro Ser Val Ala Ser Ser Thr Asn Pro Phe Gln Thr Asn Ala Arg
 225                 230                 235                 240
Gly Ala Thr Ala Ala Thr Phe Gly Thr Ala Ser Met Ser Met Pro Thr
             245                 250                 255
Gly Phe Gly Thr Pro Ala Pro Tyr Ser Leu Pro Thr Ser Phe Ser Gly
             260                 265                 270
Ser Phe Gln Gln Pro Ala Phe Pro Ala Gln Ala Ala Phe Pro Gln Gln
             275                 280                 285
Thr Ala Phe Ser Gln Gln Pro Asn Gly Ala Gly Phe Ala Ala Phe Gly
             290                 295                 300
Gln Thr Lys Pro Val Val Thr Pro Phe Gly Gln Val Ala Ala Ala Gly
 305                 310                 315                 320
Val Ser Ser Asn Pro Phe Met Thr Gly Ala Pro Thr Gly Gln Phe Pro
             325                 330                 335
Thr Gly Ser Ser Ser Thr Asn Pro Phe Leu
             340                 345

2) INFORMATION FOR SEQ ID NO:37:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:37:

Ser Ser Ser Gly Phe Ser Ser Pro Ala Phe Gly Thr Thr Ala Pro Gly
 1                   5                  10                  15
```

```
Val Phe Gly Gln Thr Thr Phe Gly Gln Ala Ser Val Phe Gly Ser Ala
             20                  25                  30

Ser Ser Ala Ala Ser Val Phe Ser Phe Ser Gln Pro Gly Phe Ser Ser
         35                  40                  45

Val Pro Ala Phe Gly Gln Pro Ala Ser Ser Thr Pro Thr Ser Thr Ser
 50                  55                  60

Gly Ser Val Phe Gly Ala Ala Ser Ser Thr Ser Ser Ser Ser Ser Phe
 65                  70                  75                  80

Ser Phe Gly Gln Ser Ser Pro Asn Thr Gly Gly Leu Phe Gly Gln
             85                  90                  95

Ser Asn Ala Pro Ala Phe Gly Gln Ser Pro Gly Phe Gly Gln Gly Gly
             100                 105                 110

Ser Val Phe Gly Gly Thr Ser Ala Ala Thr Thr Thr Ala Ala Thr Ser
         115                 120                 125

Gly Phe Ser Phe Cys Gln Ala Ser Gly Phe Gly Ser Ser Asn Thr Gly
         130                 135                 140

Ser Val Phe Gly Gln Ala Ala Ser Thr Gly Gly Ile Val Phe Gly Gln
145                 150                 155                 160

Gln Ser Ser Ser Ser Gly Ser Val Phe Gly Ser Gly Asn Thr Gly
             165                 170                 175

Arg Gly Gly Gly Phe Phe Ser Gly Leu Gly Gly Lys Pro Ser Gln Asp
             180                 185                 190

Ala Ala Asn Lys Asn Pro Phe Ser Ser Ala Ser Gly Gly Phe Gly Ser
         195                 200                 205

Thr Ala Thr Ser Asn Thr Ser Asn Leu Phe Gly Asn Ser Gly Ala Lys
         210                 215                 220

Thr Phe Gly Gly Phe Ala Ser Ser Ser Phe Gly Glu Gln Lys Pro Thr
225                 230                 235                 240

Gly Thr Phe Ser Ser Gly Gly Gly Ser Val Ala Ser Gln Gly Phe Gly
             245                 250                 255

Phe Ser Ser Pro Asn Lys Thr Gly Gly Phe Gly Ala Ala Pro Val Phe
             260                 265                 270

Gly Ser Pro Pro Thr Phe Gly Gly Ser Pro Gly Phe Gly Gly Val Pro
         275                 280                 285

Ala Phe Gly Ser Ala Pro Ala Phe Thr Ser Pro Leu Gly Ser Thr Gly
         290                 295                 300

Gly Lys Val Phe Gly Glu Gly Thr Ala Ala Ala Ser Ala Gly Gly Phe
305                 310                 315                 320

Gly Phe Gly Ser Ser Ser Asn Thr Thr Ser Phe Gly Thr Leu Ala Ser
             325                 330                 335

Gln Asn Ala Pro Thr Phe Gly Ser Leu Ser Gln Gln Thr Ser Gly Phe
             340                 345                 350

Gly
```

HUMAN PROTEIN CRITICAL FOR HIV REPLICATION

CROSS REFERENCE TO RELATED APPLICATION

This application claims benefit from provisional application Ser. No. 60/000,551, filed Jun. 27, 1995.

FIELD OF THE INVENTION

This invention pertains to a human protein required for HIV replication, nucleic acids encoding this protein, methods of using this protein, and methods of inhibiting the action of this protein.

BACKGROUND OF THE INVENTION

Human immunodeficiency virus type 1 (HIV-1) has been identified as the causative agent of AIDS (Barre-Sinoussi et al., 1983 Science 220:868–871; reviewed in Fauci (1988) Science 239:617–622). Currently, the World Health Organization estimates that between 13 and 14 million people are infected with HIV worldwide, of which one million are in the United States. The virus attacks the body's immune system and is thought to be fatal in 90% of the patients who have had AIDS for two or more years.

HIV-1 is a complex retrovirus whose life cycle is characterized by distinct kinetic phases. The key viral mediator of emergence from the initial phase, in which only non-structural proteins are produced, is the virus-encoded regulatory protein Rev, which regulates the cytoplasmic accumulation of virion genomic and structural mRNAs. Arrigo et al., 1989 J. Virol. 63: 4875–4881; Emerman et al., 1989 Cell 57: 1155–1165; Felber et al. (1989) Proc. Natl. Acad. Sci. U.S.A. 86: 1495–1499; Malim et al. 1989 Nature 338: 254–257) Kim et al., 1989 J. Virol. 63: 3708–3713; reviewed in Cullen and Greene (1989) Cell 58:423–426.

Rev is a 20-kDa protein, and is highly charged and phosphorylated. Hauber et al., 1988 J. Virol 62:4801–4804; Cochrane et al., 1989 Virology 171:264–266. It is a nuclear protein (Cullen et al. 1988 *J. Virol.* 62:2498–2501; Felber et al. (1989) Proc. Natl. Acad. Sci. U.S.A. 86:1495–1499; Perkims et al. 1989 J. AIDS 2:256–263) and accumulates in the nucleolus (Malim et al., (1989) Cell 58:205–214; Cochrane et al. 1990 J. Virol. 64:881–885).

The genome of HIV is complex and contains at least nine open reading frames. Different proteins are expressed by the production of alternatively spliced RNAs from the full-length precursor RNA. In the nucleus of the host cell, Rev binds to an HIV RNA known as the RRE (Rev-responsive element) and exports singly spliced and unspliced viral mRNAs, which contain the RRE, to the cytoplasm where they are translated into protein (Emerman et al., 1989 Cell 57: 1155–1165; Felber et al. (1989) Proc. Natl. Acad. Sci. U.S.A. 86:1495–1499; Malim et al., 1989 Nature 338: 254–257). Rev is essential for viral replication in human cells (Sodroski et al., 1986 Nature 321:412–417; Sadaie et al., (1988) Science 239:910–914; Terwillinger et al., 1988 J. Virol. 62: 655–658; Cullen and Greene (1989) Cell 58:423–426), which makes Rev an attractive target for the development of therapeutics against HIV infections and for the treatment of AIDS (Baltimore (1988) Nature 335:395–396). Preventing Rev function will prevent export and therefore translation of viral mRNAs into protein and will inhibit viral replication.

The Rev-RRE interaction, although necessary, is not sufficient for the activation of RRE-containing mRNAs. Additional cellular factor(s) interacting with Rev are necessary for Rev function (Malim et al., (1989) Cell 58:205–214; Olsen et al., (1990) Genes Dev. 4:1357–1364; Ahmed et al., 1990 Genes Dev. 4:1014–1022; Benko et al., 1990 New Biol. 2: 1111–1122). Rev mutants have been created that bind RRE but fail to function (Malim et al., (1989) Cell 58:205–214; Olsen et al., (1990) Genes Dev. 4:1357–1364). These carboxy-terminal mutants exhibit a trans-dominant negative phenotype in tissue culture cells (Malim et al., (1989) Cell 58:205–214; Venkatesh and Chinnadurai, (1990) Virology 178:327–330). Inferred from this finding is the existence of a cellular factor or factors that is necessary to effect Rev function. Several cellular proteins have been identified that bind to or interact with Rev protein, and which have been proposed to be vital for Rev function: the mammalian nucleolar protein B23 (Fankhauser et al., (1991) Mol. Cell. Biol. 11:2567–2575) YL2 (Luo et al., (1994) J. Virol. 68:3850–3856) and eIF-5A (Ruhl et al., (1993) 123:1309–1320).

Identifying the cellular factor essential for Rev function provides an important opportunity for identifying a new class of antiviral drugs. Identifying a therapeutic drug that inhibits Rev cofactor function provides an excellent opportunity for combination therapy. Because of the ability of HIV to mutate rapidly, experts agree that the best approach to combating the disease lies in simultaneous treatment with two or more therapies that target different components of the virus. There are only three approved drugs to treat HIV and AIDS, AZT, DDC, and DDI, none of which provides an effective cure, and which all work by blocking a viral enzyme called reverse transcriptase. Drugs that inhibit Rev function are likely to have toxicities distinct from those of reverse transcriptase inhibitors, and as a result will complement or act in synergy with other therapies.

Development of an effective method and composition for treatment of HIV infections is a critical goal of the pharmaceutical industry. The pharmaceutical industry has made numerous efforts to identify effective HIV drugs, with only limited success to date. It would be of great value to identify a new class of anti-HIV drug that blocks a viral or cellular target other than HIV reverse transcriptase. This target should lead to the development of a drug that is effective against viruses that are resistant to current therapy.

Development of an effective method of inhibiting the Rev effector is also likely to be useful for the treatment of other retroviruses containing Rev-like proteins such as HTLV-I and HTLV-II, HIV-1, HIV-2, HTLV-I and HTLV-II, although associated with different pathological processes, all require translation of incompletely spliced mRNA species for production of viral structural genes. Rev is conserved in all HIV and simian immunodeficiency virus isolates (Malim et al., (1989) Proc. Natl. Acad. Sci. U.S.A. 86:8222–8226; Holland et al., (1990) J. Virol. 64:5966–5975). RREs from different primate immunodeficiency viruses can be functionally interchanged to some extent (Malim et al., (1989) Proc. Natl. Acad. Sci. U.S.A. 86:8222–8226). Similar to Rev, Rex-I is essential for virus replication (Rosenblatt et al., (1988) Science 240:916–919). Rex-I facilitates the cytoplasmic accumulation of unspliced or singly spliced viral mRNAs that encode Gag, Pol, and Env structural proteins (Hidaka et al. (1988) EMBO J. 7:519–523; Inoue et al., (1987) Proc. Natl. Acad. Sci. U.S.A. 84:3653–3657; Ohta et al., (1988) J. Virol. 62:4445–4451; Seiki et al., (1983) Proc. Natl. Acad. Sci. U.S.A. 85:3618–3622). Rex-I and Rex-II proteins and the $Rex_I RE$ and $Rex_{II}RE$ are entirely interchangeable and Rex-II can replace Rev in HIV-I (Kim et al., (1991) 65:405–414). Rev, however, is unable to replace Rex-II in the HTLV-II system (Kim et al., (1991) 65:405–414).

It is likely that the same cellular factor(s) required for export of HIV-1, HIV-2, HTLV-I, and HTLV-II structural RNAs interacts with both the Rev proteins of HIV-1 and HIV-2 and the Rex proteins of HTLV-I and HTLV-II (Olsen et al., (1990) Genes Dev. 4:1357–1364). Transdominant repressors of Rex-I function are also transdominant suppressors of Rev function (Rimsky et al., (1989) Nature 335:738–740). Similarly, Rev inhibits Rex function in a dominant manner when the Rev responsive subregion of the RRE is deleted (Ahmed et al., (1990) Genes Dev. 4:1014–1022).

Drug development often relies on the screening of a large number of potential inhibitors before a specific lead compound inhibitor is found. Assays developed for such screens are complex and must mimic the physiological activity of the target protein. Thus, it is critical for the development of these screens to define the proteins involved in the targeted process and to have discovered a means of purifying the necessary components of the assay for use in the assay. In addition, it is useful to have clones for the protein components of the assay to facilitate the production of the components. Therefore, there is a need in the art to identify viral and cellular constituents, preferably polypeptides, that can serve as useful targets for drug intervention, and for methods and compositions for identifying useful anti-viral agents and treating viral infections.

SUMMARY OF THE INVENTION

The present invention provides a human cellular polypeptide, termed human Rev interacting polypeptide ("hRIP"), that is necessary for HIV replication. The polypeptide has a molecular mass of about 59 kDa, having the sequence set forth in FIG. 2a (SEQ ID NO:1). hRIP is the cellular cofactor required to mediate the Rev response. hRIP binds HIV Rev protein and is essential for Rev activity. The invention also includes nucleic acid sequences encoding hRIP, as well as DNA vectors and transformed cells suitable for recombinant expression of this polypeptide.

In one aspect, the present invention encompasses methods for inhibiting Rev function in a human cell, comprising contacting the cell with an agent that selectively interferes with the hRIP activity.

In another aspect, the invention provides a method for high-throughput screening of large numbers of test compounds, to identify an agent useful in the treatment of viral diseases in mammals. The method is carried out by exposing hRIP to Rev or Rev-RRE complex in the presence of at least one test compound, followed by identifying those test compounds that inhibit the binding of Rev to hRIP.

BRIEF DESCRIPTION OF THE DRAWINGS

FIG. 1 is a schematic diagram comparing the effect of mutations on Rev effector function and their effect on hRIP binding. Relevant sequences of wild type Rev (SEQ ID NO:3), Rev mutants (M10 (SEQ ID NO:4), M20 (SEQ ID NO:5), M22 (SEQ ID NO:6), M25 (SEQ ID NO:7), M27 (SEQ ID NO:8), M29 (SEQ ID NO:9), and M36 (SEQ ID NO:10)), and wildtype HTLV-I Rex (SEQ ID NO:11) are shown. The leucines within the Rex effector domain that align with Rev are underlined. Rev function was measured by gtat and p24 assays. Binding of Rev and Rex derivatives to hRIP was determined in a yeast two-hybrid assay. LacZ activity is reported as −, ±, +, ++, and +++; more pluses signify greater LacZ activity, which indicates a greater degree of interaction between hRIP and Rev and Rex derivatives.

FIG. 2a shows the DNA (SEQ ID NO:2) and predicted amino acid sequence (SEQ ID NO:1) of a full-length hRIP cDNA clone. The N-terminal potential zinc finger is underlined and the relevant cysteines are boxed. In the nucleoporin homology region the FG repeats are boxed and the other repeats underlined.

FIG. 2b shows a northern blot of polyA$^+$-enriched HeLa RNA probed with a $^{32}$P-labeled hRIP DNA fragment. The arrow indicates the migration of the 2.6 kb hRIP mRNA. The migration of the molecular mass markers is indicated on the left.

FIG. 2c shows a protein blot in which polypeptides in a HeLa nuclear extract (Immunoblot) were resolved by SDS-PAGE, transferred to nitrocellulose, and probed with an affinity purified α-hRIP antibody. Mobility of the detected polypeptide is compared with that of an aliquot of $^{35}$S-labeled in vitro translation product of a full-length hRIP clone (IVT). The migration of the molecular mass markers is indicated on the left.

FIG. 2d shows proteins in the National Institutes of Health's National Center for Biotechnology information protein database with homology to the hRIP potential zinc-finger (SEQ ID NOs: 12 to 19). Alignment for each protein begins at the indicated residue. The cysteines are in bold. The residues conserved in four or more proteins are boxed and shaded.

FIG. 2e shows that hRIP contains short amino acid repeat motifs (SEQ ID NOs: 20 to 35). The numbers indicate the position of the repeats in the hRIP sequence. Amino acids conserved between repeats are in bold.

FIG. 2f shows alignment of hRIP (SEQ ID NO:36) and CAN protein/nup214 (SEQ ID NO:37), a nucleoporin. FG repeats and other aligned phenylalanines are boxed.

DETAILED DESCRIPTION OF THE INVENTION

Figure 3A:
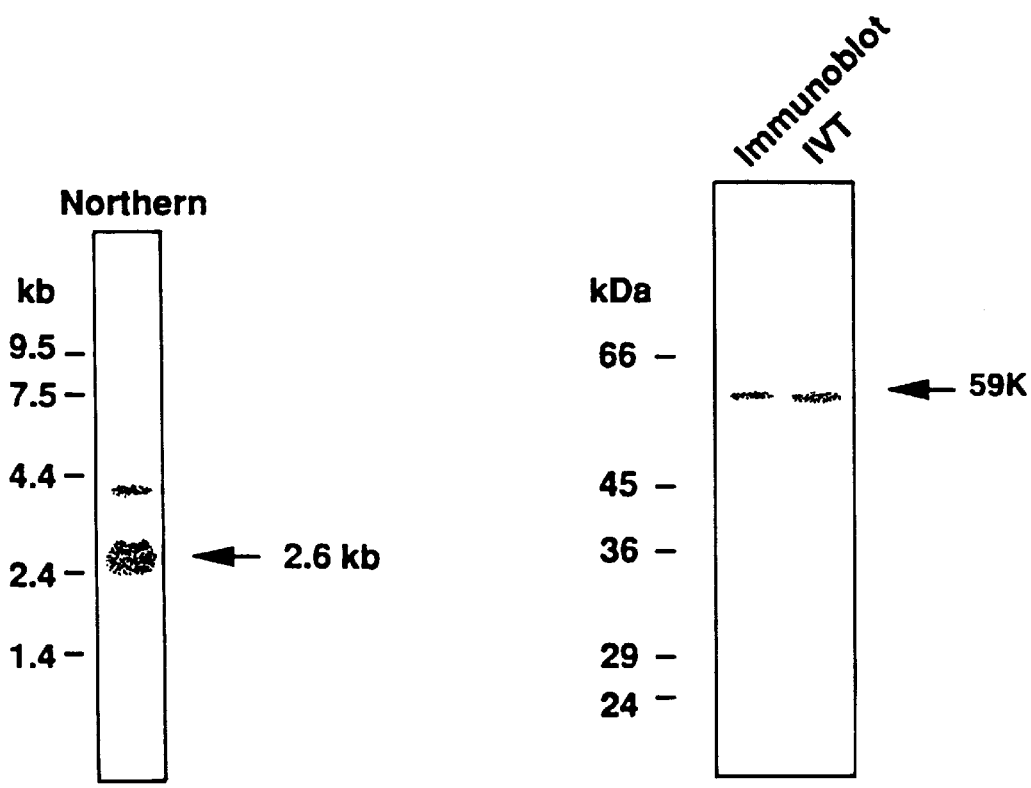
FIG. 3a shows the intracellular distribution of hRIP in fractionated HeLa cells. CE, cytoplasmic extract; NE, nuclear extract; NPE, nuclear pellet extract. Each fraction was separated by 10% SDS-PAGE and then immunoblotted with α-hRIP antibody. The migration of the molecular mass markers is indicated on the left.
Figure 3A:
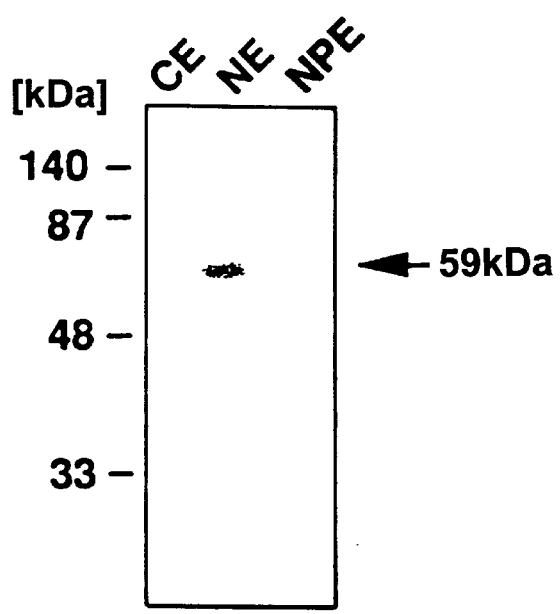

All patent applications, patents, and literature references cited in this specification are hereby incorporated by reference in their entirety. In case of conflict, the present description, including definitions, will control.

Definitions

1. "Rev" is an essential component of human immunodeficiency virus (HIV). Rev contains at least two essential protein domains: an RNA binding domain and an "activation domain."

2. The Rev "activation domain" indicates the carboxy-terminal domain of the Rev protein defined functionally by mutants such as M10 that alter Rev activity without affecting RNA binding.

3. "hRIP" as used herein refers to cellular polypeptides or complexes of polypeptides that are required for Rev "cofactor activity" by virtue of their association with the Rev "activation domain." Such polypeptides are distinguished from any polypeptides previously known to be Rev binding proteins. These polypeptides bind with lower affinity or not at all to activation domain mutants such as M10. hRIP may be recombinant or purified from natural sources, and may include structural or functional hRIP homologues as defined below.

4. "Functional homology" between hRIP polypeptides or complexes of polypeptides indicates that one or more biochemical properties specific to hRIP are shared. Examples of such properties are: the ability to specifically modulate the activity of Rev protein, and the capacity to specifically bind the activation domain of Rev protein under conditions as described herein.

5. "Sequence homology" is used herein to describe the relatedness of hRIP from different sources. "Substantial" sequence homology means that about 70%, more preferably at least about 80%, and most preferably at least about 90% of the two sequences are identical. The level of sequence homology may also be defined functionally, as in, e.g., the stringency of hybridization conditions under which the two sequences effectively or substantially hybridize. "Stringent" hybridization conditions are defined herein as 0.1×SSC at 65° C.

6. An "isolated" polypeptide or nucleic acid is defined as one that is purified or separated from at least some of the material with which it is associated in its natural state. Generally, an isolated polypeptide constitutes at least about 1%, preferably at least about 10%, and more preferably at least about 50% by weight of the total protein in a given sample. Included in the polypeptide weight are alternative forms such as differentially glycosylated or phosphorylated or otherwise post-translationally modified forms. An "isolated" nucleic acid sequence is present as other than a naturally occurring chromosome or transcript in its natural state, and typically is removed from at least some of the proteins with which it is normally associated with on a natural chromosome.

A partially pure nucleotide sequence constitutes at least about 5%, preferably at least about 30%, and more preferably at least about 90% by weight of total nucleic acid present in a given fraction.

The present invention is based on the discovery of a novel cellular cofactor required to mediate the Rev-response, hRIP, which interacts with the Rev activation domain. Prior to the work reported herein (see Example 1 below), no biochemical or genetic evidence had indicated the identity of such a polypeptide. The discovery and characterization of this polypeptide factor implicate this protein as an important target for the development of new methods and compositions for treatment of viral infections. The present invention is thus directed towards interference with Rev and hRIP activity.

hRIP Polypeptides and Nucleic Acids

The present invention provides hRIP, which comprises a polypeptide having a molecular mass of about 59 kDa. The polypeptide may be isolated by virtue of its affinity to HIV Rev or HTLV-I Rex protein (see Example 1 below), by the use of chromatographic procedures that take advantage of physico-chemical characteristics of the polypeptide, or by affinity to hRIP-specific antibodies. The polypeptide may also be purified from translation products of subunit genes (see Example 1 below), or from recombinantly produced hRIP. It is also contemplated that additional hRIP polypeptides or any analogs thereof will be identified using methods disclosed herein, and will be used in practicing the present invention.

It is important that the hRIP protein disclosed here is distinct from the previously identified Rev binding proteins. All of these factors, eIF-5A, B23 and YL2, are unrelated to hRIP by sequence analysis. Two of these proteins, B23 and YL2, bind to a different region of the Rev protein (the RNA binding domain of Rev, not the activation region). eIF-5A is thought to bind to the activation region, but there is no evidence that activation region mutants such as M10 block eIF-5A binding. It was thus surprising and unexpected to discover hRIP, a protein which has the expected characteristics of the cellular effector for the HIV Rev protein.

The present invention also encompasses nucleic acid sequences that encode hRIP. Methods for determining the relevant nucleic acid sequences are described in Example 1 below, and the deduced amino acid sequences of one hRIP gene is shown in FIG. 2a (SEQ ID NO:1). The present invention encompasses hRIP DNA and RNA sequences, and sense and antisense sequences. hRIP-encoding sequences according to the present invention may be modified by transitions, transversions, deletions, insertions, or other modifications such as alternative splicing. The invention also encompasses genomic hRIP sequences and hRIP gene flanking sequences, including hRIP regulatory sequences. Nucleic acid sequences encoding hRIP polypeptides may also be associated with heterologous sequences, including promoters, enhancers, response elements, signal sequences, polyadenylation sequences, introns, 5'- and 3'-noncoding regions, and the like. Other useful heterologous sequences can be obtained according to the methods described herein by those skilled in the art. Furthermore, the nucleic acids can be modified to alter stability, solubility, binding affinity and specificity. For example, hRIP encoding sequences can be selectively methylated. The nucleic acid sequences of the present invention can also be modified with a label capable of providing a detectable signal, either directly or indirectly. Exemplary labels include radioisotopes, fluorescent molecules, biotin, and the like.

In general, nucleic acid manipulations according to the present invention use methods that are well known in the art, as disclosed in, e.g., *Molecular Cloning, A Laboratory Manual* (2nd Ed., Sambrook, Fritsch and Maniatis, Cold Spring Harbor), or *Current Protocols in Molecular Biology* (Eds. Ausubel, Brent, Kingston, Moore, Seidman, Smith and Struhl, Greene Publ. Assoc., Wiley-Interscience, New York, N.Y., 1992).

The invention also provides vectors comprising nucleic acids encoding hRIP or hRIP analogs. A large number of vectors, including plasmid and fungal vectors, have been described for expression in a variety of eukaryotic and prokaryotic hosts. Advantageously, vectors may also include a promoter operably linked to the hRIP coding portion. The encoded hRIP can be expressed by using any suitable vectors and host cells, using methods disclosed or cited herein or otherwise known to those skilled in the relevant art. The particular choice of vector/host is not critical to the invention.

Vectors will often include one or more replication systems for cloning or expression, one or more markers for selection in the host, e.g., antibiotic resistance, and one or more expression cassettes. The inserted hRIP coding sequences can be synthesized, isolated from natural sources, prepared as hybrids, etc. Ligation of the coding sequences to the transcriptional regulatory sequences can be achieved by known methods. Suitable host cells can be transformed/transfected/infected by any suitable method including electroporation, calcium phosphate- or DEAE-mediated DNA uptake, fungal infection, microinjection, microprojectile, or other established methods.

Appropriate host cells include bacteria, archaebacteria, fungi, especially yeast, and plant and animal cells, especially mammalian cells. Of particular interest are *E. coli, B. subtilis, Saccharomyces cerevisiae*, SF9 cells, C129 cells, 293 cells, Neurospora, CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced hRIPs.

Nucleic acids encoding hRIP polypeptides can also be introduced into cells by recombination events. For example, such a sequence can be microinjected into a cell, and thereby effect homologous recombination at the site of an endogenous gene encoding hRIP, an analog or pseudogene thereof, or a sequence with substantial identity to an hRIP-encoding gene. Other recombination-based methods such as nonhomologous recombinations, deletion of endogenous gene by homologous recombination, especially in pluripotent cells, can also be used.

hRIP polypeptides and the nucleic acids encoding these polypeptides can be derived from any eukaryotic cell, including mammalian and non-mammalian cells, and can be proteins with substantial functional or sequence homology to human hRIPs. Based on the disclosure of the current invention, hRIPs other than those explicitly described herein can be identified and isolated by methods that are well-known in the art. These include: antibody cross reactivity; PCR amplification from genomic or cDNA using degenerate oligonucleotide probes derived from the hRIP sequences disclosed herein; low-stringency hybridizations using similar human probes; and, finally, functional cloning, in which a cDNA expression library derived from another species is used to transform and complement an absent or defective hRIP function in human cells.

The present invention encompasses hRIP proteins purified from wild-type and genetically altered strains of human cells, as well as hRIPs of all eukaryotic origins recombinantly produced in a non-native context. In one embodiment, a baculovirus expression system permits the recombinant hRIP to be modified, processed, and transported within a eukaryotic system. In another embodiment binding of hRIP complexes to Rev is performed in a reconstituted cell-free system using partially purified or substantially purified components. For example, hRIP complexes, or components thereof, can be adsorbed to the surface of a microtiter plate, and incubated with Rev protein and radiolabelled RRE RNA. Functional binding of Rev-RRE complex to hRIP components will result in the association of detectable radioactivity with the plate.

The hRIP polypeptides of the invention isolated from any source can be modified by methods known in the art. For example, hRIP polypeptides may be phosphorylated or dephosphorylated, glycosylated or deglycosylated, and the like. Especially useful are modifications that alter hRIP solubility, membrane transportability, stability, and binding specificity and affinity. Some examples include fatty acid-acylation, proteolysis, and mutations in Rev interaction domains that stabilize or destabilize binding.

The hRIP polypeptides of the invention can also be modified with a label capable of providing a detectable signal, for example, at a heart muscle kinase labeling site, either directly or indirectly. Exemplary labels include radioisotopes, fluorescent compounds, etc. Such labeled hRIPs thereof find use, for example, as probes in expression screening assays for proteins that interact with hRIP, or in assays for hRIP binding to HIV Rev or to HTLV Rex.

Identification of Functionally Important hRIP Domains and Binding Partners

The polypeptides, protein complexes, and nucleic acids sequences of the present invention find use in the discovery, design, and development of pharmaceutically useful antiviral agents. The following embodiments of the present invention are directed towards elucidating epitopes and interactions of hRIP polypeptides that can be selectively interfered with in a therapeutically beneficial manner.

In one embodiment, the sequence of hRIP is used to design synthetic peptides comprising portions of the sequence. These peptides range from about 15 to about 50 amino acids in length. Peptides under 60 amino acids in length can be synthesized routinely using commercially available automated synthesizers. The peptides are then added to a cell-free assembly reaction containing, e.g., immobilized hRIP complex and soluble radiolabelled Rev or Rev-RRE complex. Determining which synthetic peptides inhibit some interaction of hRIP with other factors, using routine experimentation, is used to identify different functional domains or epitopes of hRIP subunits. For example, a peptide (derived from hRIP) that is found using the above-described method to inhibit the binding of Rev to hRIP is likely to represent a region of hRIP that interacts directly with Rev. In a similar manner, associational domains of hRIP that are involved in interactions between hRIP and other components can be systematically identified. These peptides may themselves constitute useful therapeutic reagents, or may serve as the basis for the design and formulation of pharmacologically active compositions.

In another embodiment, important functional domains of hRIPs are identified using classical and reverse genetic methods that are well-known in the art. For example, a nested set of deletion mutants can be prepared from any known hRIP sequence. In this embodiment, progressively longer amino-terminal and carboxy-terminal deletions (such as those shown in Example 1) can be engineered in a particular hRIP sequence. The resulting set of mutant sequences can be individually expressed in eukaryotic cells under conditions in which the wild-type version of the hRIP is not expressed. By monitoring the function of each mutant, it is possible to identify different regions of each hRIP polypeptide that are critical for function i.e. functional domains or epitopes. Based on such studies, using methods that are well-known in the art, it is possible to selectively introduce defined mutations into different regions of the polypeptide, and perform a similar functional analysis.

Identification of important structural and functional domains of hRIP according to the present invention enables the design and production of useful hRIP-derived nucleic acid and peptide-based compounds. For example, fusion proteins can be produced between an important hRIP domain and, e.g., an enzymatically active fragment of an RNA endonuclease. The resulting fusion protein, which can be produced in a eukaryotic cell following introduction into the cell of the hybrid DNA operably linked to an expression vector, finds use in modulating hRIP-dependent gene expression. Other useful hRIP fusion partners include sequences useful for immobilization. For example, sequences derived from glutathione-S-transferase (GST) provide a binding site for immobilized glutathione, and sequences that form an epitope recognized by an available monoclonal antibody (e.g. 12CA5 monoclonal antibody) provide a binding site for the immobilized antibody.

In another example, particular serine, threonine, or tyrosine residues in the hRIP sequence may be identified as functionally important sites for phosphorylation of hRIP. See, e.g., methods disclosed in Roberts et al. (1991) Science 253, 1022–1026, and in Wegner et al. (1992) Science 256, 370–373. Phosphorylation of hRIP may be involved in modulating the expression of genes. Identification of these residues will enable, first, the radiolabelling of hRIP subunits with $\gamma$-32P-ATP. Furthermore, if phosphorylation of a particular residue is necessary for activity, phosphorylation inhibitors can be designed to block activity.

The nucleic acids encoding hRIP can also be used to identify other nuclear factors that interact with hRIP. In this embodiment, a yeast cDNA library containing fusion genes of cDNA joined with DNA encoding the activation domain of a transcription factor (e.g. Gal4) is co-transfected with fusion genes encoding a portion of hRIP and the DNA binding domain of a transcription factor. Clones encoding hRIP binding proteins are able to complement the transcription factor and are identified through transcription of a reporter gene. See, e.g., Example 1 and Fields and Song (1989) *Nature* 340: 245–246 and Chien et al. (1991) *Proc. Natl. Acad. Sci. USA.* 88: 9578–9582. It is contemplated that these additional binding partners for hRIP will provide additional targets for antiviral drug therapy.

Anti-hRIP Antibodies

The present invention encompasses antibodies that are specific for hRIP polypeptides identified as described above. The antibodies may be polyclonal or monoclonal, and can distinguish hRIP from other nuclear proteins, discriminate hRIP from different species, identify associational or other functional domains, and the like. Such antibodies are conveniently made using the methods and compositions disclosed in Harlow and Lane, *Antibodies, A Laboratory Manual*, Cold Spring Harbor Laboratory, 1988, and other references cited herein, as well as immunological and hybridoma technologies known to those in the art. Where natural or synthetic hRIP-derived peptides are used to induce an hRIP-specific immune response, the peptides can be conveniently coupled to a suitable carrier such as keyhole limpet hemocyanin and administered in a suitable adjuvant such as Freunds. Preferably, selected peptides are coupled to a lysine core carrier substantially according to the methods of Tam (1988) *Proc. Natl. Acad. Sci. USA* 85, 5409–5413. The resulting antibodies may be modified to a monovalent form, e.g. Fab, FAB', or FV. Anti-idiotypic antibodies, especially internal imaging anti-idiotypic antibodies, can also be prepared using known methods.

In one embodiment, purified hRIP is used to immunize mice, after which their spleens are removed, and splenocytes are used to form cell hybrids with myeloma cells and to obtain clones of antibody-secreting cells according to techniques that are standard in the art. The resulting monoclonal antibodies are screened using in vitro assays such as those described above for the following activities: binding to hRIP, and inhibiting the interaction between hRIP and Rev. In another embodiment, the hRIP is used as an immunogen as above, and the resulting monoclonal antibodies are screened for their activity in inhibiting the in vitro assembly of any component of an hRIP complex.

Anti-hRIP antibodies can be used to identify and quantify hRIP components, using immunoassays such as ELISA, EMIT, CEDIA, SLIFA, and the like. Anti-hRIP antibodies can also be used to block the transcriptional function of hRIP by inhibiting formation of complexes between hRIP or between assembled hRIP complexes and other components, or by immunodepleting cell extracts or binding reactions of hRIP components. In addition, these antibodies can be used to identify, isolate, and purify hRIPs from different sources, and to perform subcellular and histochemical localization studies (see Example 1).

High-Throughput Drug Screening

The present invention encompasses the identification of agents useful in modulating viral gene expression, particularly the expression of HIV genes by Rev in an hRIP-dependent manner. In a preferred embodiment, a high-throughput screening protocol is used to survey a large number of test compounds for their ability to interfere with hRIP-dependent processes.

Potential inhibitory compounds are screened from large libraries of synthetic or natural compounds. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant, and animal extracts are available from, e.g., Pan Laboratories (Bothell, Wash.) or MycoSearch (North Carolina), or are readily producible. Additionally, natural and synthetically produced libraries and compounds are readily modified through conventional chemical, physical, and biochemical means.

Potential inhibitory proteins can also be generated using the yeast two-hybrid system referred to above. cDNA from any source can be joined with DNA encoding the activation domain of a transcription factor (e.g., Gal4) and cotransfected with fusion genes encoding a portion of hRIP and the DNA binding domain of a transcription factor. Clones encoding hRIP binding proteins are able to complement the transcription factor and are identified through transcription of a reporter gene. The structural features of these proteins can then be used as models or templates for the synthesis of small molecule drugs that can be assayed for their ability to interfere with hRIP function.

Useful inhibitory agents are identified with a range of assays employing hRIP or hRIP-encoding nucleic acids. As examples, protein binding assays, nucleic acid binding assays, gel shift assays, cell-based assays, and the like are useful approaches. Preferably, hRIP polypeptides as provided by the present invention can be used in in vitro binding assays with either Rev alone, or with a combination or subcombination of Rev and the RRE RNA. Alternatively, cell-based assays as described in Example 1 can be used to assay inhibitors of hRIP-dependent function.

For example, hRIP can be immobilized on microtiter dishes using methods that are standard in the art. The plates are then exposed to radiolabelled Rev or Rev peptides, or to Rev or Rev peptides and radiolabelled RRE, e.g., $^{32}$P-Rev or $^{32}$P-RRE in the absence or presence of candidate compounds. Conversely, Rev or Rev peptides can be immobilized, and incubated with radiolabelled hRIP or hRIP peptides in the absence or presence of candidate compounds. Oligonucleotides comprising Rev target sequences (RRE) can be used in conjunction with Rev and hRIP (see Example 2 below). Positive "hit" compounds are those that inhibit hRIP-Rev interaction. In these cases, incubation, washing, and radioactivity detection steps can be automated, allowing the screening of a large number of compounds, preferably at least about 1000 compounds per week.

Once a particular test compound has been identified as described above, its activity is then confirmed by adding it to a cell-based Rev assay, and measuring its effect on hRIP-mediated activated transcription (see, e.g., Zapp, Stern and Green (1993) Cell 74:969–978).

It is also contemplated that a useful agent may interfere with the function of hRIP but not with hRIP-Rev complex assembly. To screen for such compounds, other functional assays are used, e.g., cell-based reactions alone, or in vitro screens using hRIP and other factors identified using hRIP or hRIP sequences as disclosed herein.

It will be understood that a compound that interferes with any aspect of hRIP assembly or function is a likely candidate for an antiviral drug. Thus, in a manner similar to that described above for Rev-hRIP binding paradigm, binding assays can be routinely devised that measure the interaction of one or more hRIP polypeptides with other necessary factors.

Finally, a test compound identified as described above is tested for two properties: 1) its ability to inhibit viral growth; and 2) its lack of effect on the growth of mammalian cells. Viral growth is measured by any method well-known in the art, e.g., p24 or reverse transcription assays. The lack of effect of a test compound on mammalian cells is tested by any method well-known in the art, e.g., XTT, MTT, or $^3$H-thymidine assays.

According to the present invention, useful agents may be found within numerous chemical classes, though typically they are organic compounds, and preferably small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds can be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxyl terminus, e.g., for the amino group, acylation or alkylation, and for the carboxyl group, esterification or amidification, or the like. Other methods of stabilization may include encapsulation, for example, in liposomes, etc.

Therapeutic Applications

For therapeutic uses, e.g., the treatment of viral infections in mammals, the compositions and agents disclosed herein can be administered in a pharmaceutically acceptable formulation by an oral, transdermal, intranasal, rectal, intravenous, intramuscular, or subcutaneous route. Alternatively, the compositions can comprise creams, ointments, lotions, or sprays for topical use. Generally, the amount administered will be empirically determined, typically in the range of about 10 to 1000 pg/kg of the recipient. For peptide agents, the concentration will generally be in the range of about 100 to 500 ug/ml in the dose administered. Other additives may be included, such as stabilizers, bactericides, etc. These additives will be present in conventional amounts.

The present invention is further described and will be better understood by referring to the working Examples set forth below. These non-limiting Examples are to be considered illustrative only of the principles of the invention. Further, since numerous modifications and changes will readily occur to those skilled in the art, it is not desired to limit the invention to the exact construction and operation shown and described. Accordingly, all suitable modifications and equivalents may be used and will fall within the scope of the invention and the appended claims.

EXAMPLES

Example 1

Identification of hRIPs

The studies described below were performed to identify and isolate HIV Rev cofactors from mammalian cells.

Activity of Rev Mutants

The Rev mutants of FIG. 1 (with specific amino acid substitutions) have been previously analyzed for Rev activity and the results of the gTat and p24 assays are from Malim et al., (1991) J. Virol. 65:4248–4254).

hRIP Binding Assays

Binding of Rev and Rex derivatives to hRIP was determined in a yeast two-hybrid assay. Full-length HIV-1 Rev, the Rev mutants of FIG. 1, and HTLV-I Rex proteins were fused to LexA (1–202) in the vector pEG202 (Gyuris et al., (1993) Cell 75:791–803) by PCR, using appropriate primers and templates (Malim et al., (1991) J. Virol 65:4248–4254). The two hybrid screen was performed using an activation domain-tagged HeLa cDNA library (Gyuris et al., (1993) Cell 75:791–803) and the LexA-Rex construct as a bait in the yeast strain EGY48 (Gyuris et al., (1993) Cell 75:791–803). Primary positive plasmids were recovered and retransformed into EGY48 expressing LexA, LexA-Rev or LexA-RevM10 and containing the lacZ reporter plasmid pSH 18-34 (Gyuris et al., (1993) Cell 75:791–803). Two clones were recovered from $1.2\times10^7$ primary transformants, which both contained a C-terminal portion of hRIP starting at amino acid 361 and 388, respectively. For the analysis of Rev mutants, EGY48 containing an integrated version of pSHI8-34 was transformed with the larger of the two hRIP clones and various LexA-Rev mutant fusions and colonies scored for lacZ expression on selective Gal/Raf X-Gal plates. FIG. 1 demonstrates a perfect correlation between Rev activity and hRIP binding: all mutants retaining Rev activity bound hRIP, whereas all inactive mutants failed to interact.

Cloning and sequencing of hRIP DNA

A size selected human placental cDNA library (ATCC 77399) was screened with an hRIP DNA fragment by standard methods and two overlapping λ clones were recovered. Both clones were sequenced on both stands using Sequenase and nested exonuclease III deletions. Sequence analysis indicated that the clones contained a 1686 bp open reading frame. This nucleic acid sequence (SEQ ID NO:2) and the putative amino acid sequence (SEQ ID NO:1) it encodes are shown in FIG. 2a.

Northern Blot Analysis

10 μg polyA+-enriched HeLa RNA were separated on a 1.2% denaturing agarose gel, blotted to a nylon filter, and probed with the $^{32}$P-labeled EcoRI-Sac1 fragment of hRIP. The major band detected, of 2.6 kb, corresponded closely to the size of the cDNA containing the 1686 bp open reading frame which codes for hRIP.

hRIP Antibody Production

A polyclonal serum against hRIP was raised by expressing amino acids 361 to 562 as a polyhistidine fusion protein in E. coli. The protein was purified on Ni-agarose (Qiagen) and injected into rabbits using standard procedures (BABCO). The serum was subsequently affinity purified against the antigen crosslinked to an Affigel column (BioRad).

Immunoblot/In Vitro Translation

30 μg of Hela nuclear extract were loaded on a 10% SDS polyacrylamide gel. After separation, the proteins were transferred to a PVDF membrane and first developed as an immunoblot with α-hRIP primary and goat α-rabbit secondary antibodies using the ECL detection system (Amersham). The membrane was then exposed to x-ray film overnight to visualize the $^{35}$S-labeled protein (IVT). $^{35}$S-labeled in vitro translation products of a full-length hRIP clone were generated by methods well known in the art. In vitro transcription/translation of the hRIP cDNA resulted in a 59 kDa polypeptide, indistinguishable in size from the HeLa cell polypeptide detected by immunoblotting with an affinity-purified α-hRIP antibody (FIG. 2c). The size of the hRIP polypeptide (59 kDa) is consistent with the molecular weight predicted from the hRIP open reading frame (58.3 kDa).

Zinc Finger Homology

Figure 2D:
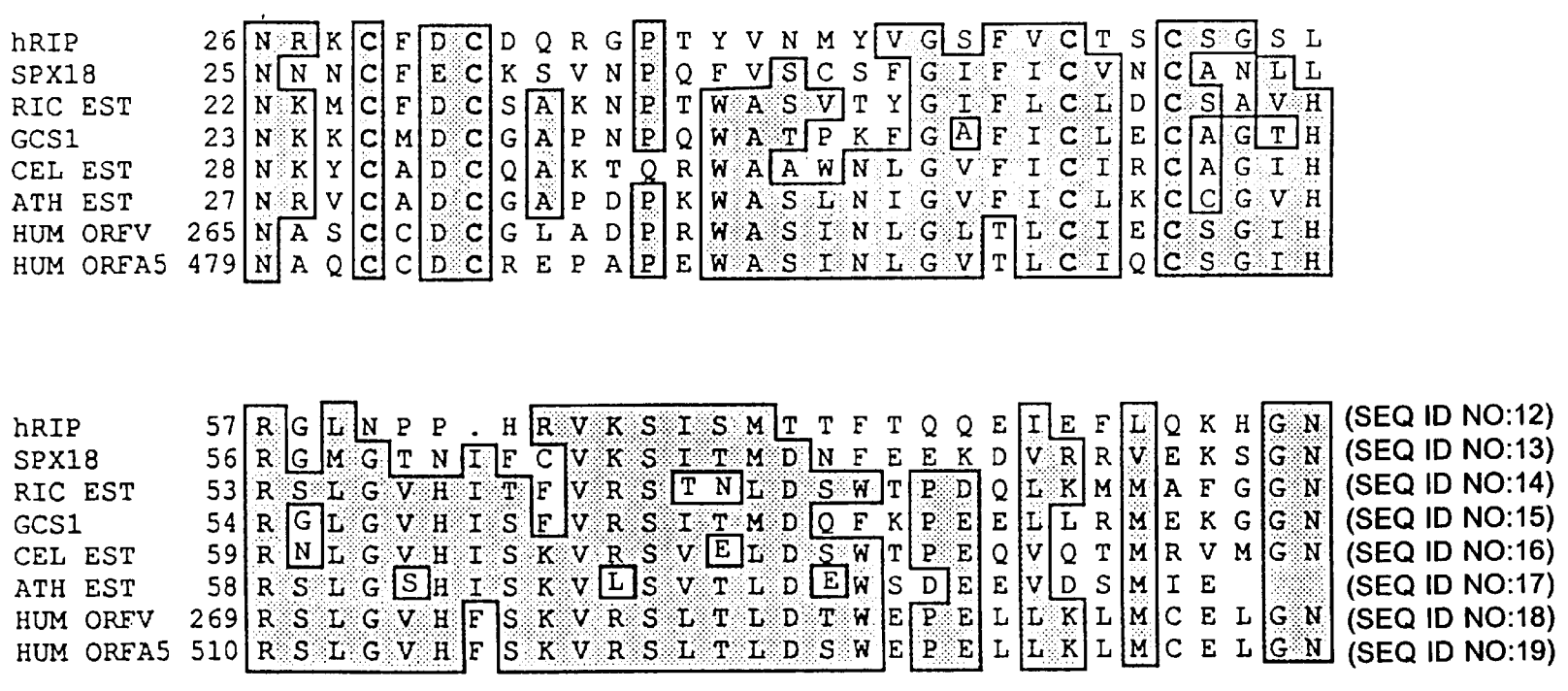

For the alignment of hRIP to other proteins in the National Institute of Health's National Center for Biotechnology Information protein and nucleic acid database, a Blast search was conducted with the hRIP N-terminus and subsequently with the GCS1 sequence. Several significant sequence motifs emerged. At the N-terminus, two pairs of cysteine residues define a class of zinc-finger that was first recognized in several yeast proteins but is present in proteins from yeast to man (FIG. 2d). Proteins containing the zinc finger motif were then aligned using the Pileup program of the GCG sequence analysis software package. hRIP and nup214 were aligned using the Fasta program from the GCG package. Accession numbers are those to be used to retrieve the sequences from the National Institutes of Health's National Center for Biotechnology Information non-redundant protein and nucleic acid database. SPX18 is a sporulation induced gene from S. cerevisiae (accession #M90351), RIC EST, CEL EST and ATH EST are expressed sequence tags from Rice (Oryza sativa, accession #D24983), C. elegans (accession #M75823) and Arabidopsis thaliana (accession #T04032), respectively. GCS1 is involved in the transition from stationary phase to cell proliferation in yeast (Ireland et al., (1991) EMBO J. 13:3812–3821) (accession #L24125). HUM ORFV and HUM ORFAS are two human open reading frames of unknown function (accession #D26069 and #D30758). There also exist in the putative amino acid sequence ten XXFG repeats (FIG. 2e; SEQ ID NOs:20–29) that are reminiscent of the GLFG and XFXFG repeats found in most yeast and some mammalian nucleoporins. One of the highest homology scores (20% identify, 48% similarity) is achieved with the human CAN protein/nup214, a 214 kDa nucleoporin that contains several degenerate FG repeats, and it is with these signature repeats that the two proteins align (FIG. 2f, SEQ ID NOs:36 and 37). Other proteins identified in the National Institute of Health's National Center for Biotechnology Information nonredundant protein and nucleic acid database search include the nuclear envelope protein POM121 and nup153. hRIP also contains several additional short repeats (FIGS. 2 a, e), which is again typical of nucleoporins.

hRIP Deletion Mutants

Figure 2G:
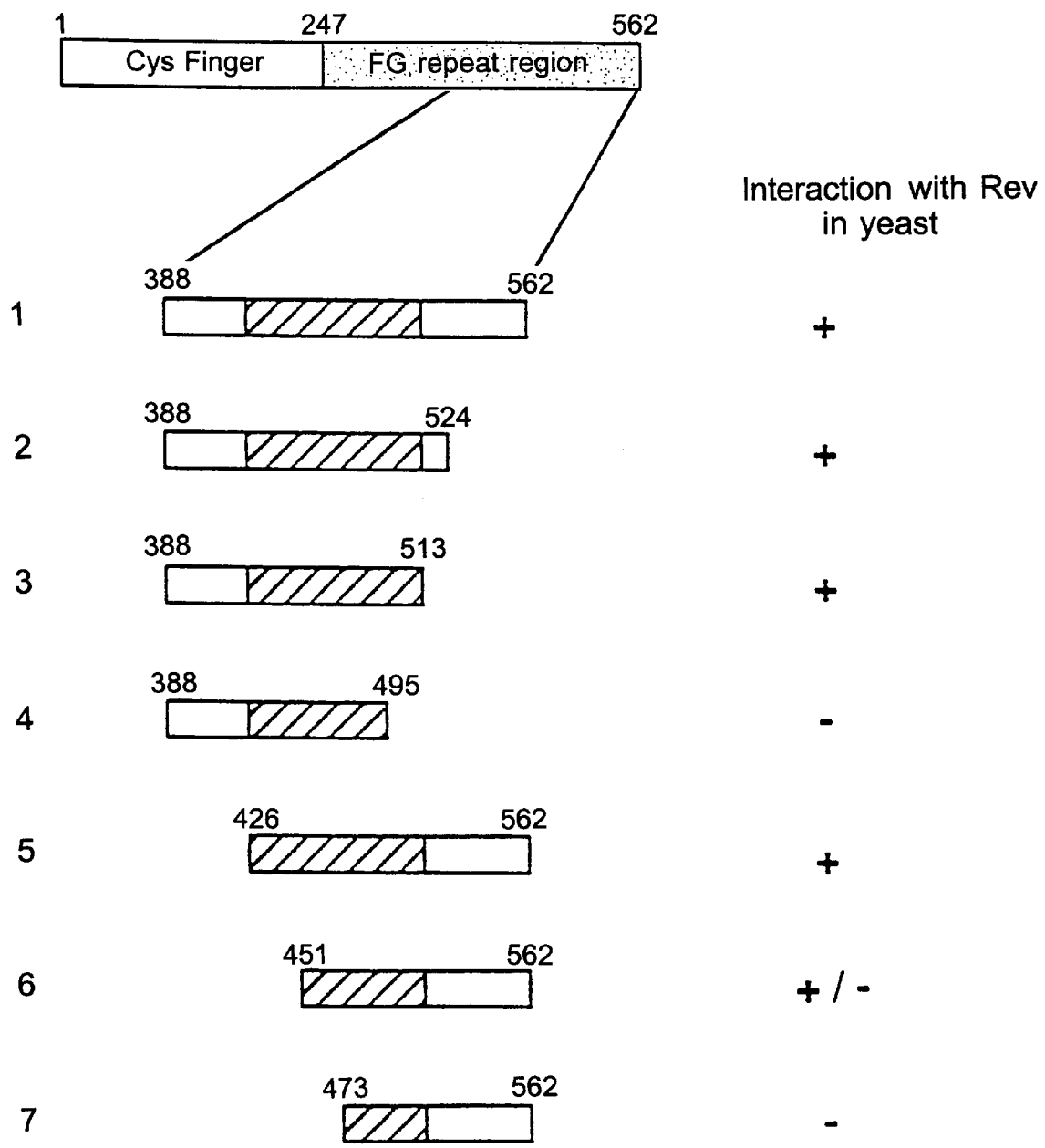
FIG. 2g shows the hRIP region that interacts with Rev. A schematic diagram of hRIP and deletion mutants of hRIP is shown. Activation region-tagged versions of these derivatives were tested for interaction with Rev in the yeast two-hybrid assay and the results are indicated on the right. The hatched region indicates the minimal boundaries of Rev interaction.

N-terminal deletions of the FG repeat regions were constructed using appropriate oligonucleotides and hRIP as a template in PCR reactions. For the C-terminal deletions, exonuclease III deletions used for sequencing were amplified and both derivatives were cloned back in-frame into the two-hybrid vector pJG4-5 (Gyuris et al. Cell (1993) 75:791–803) using the unique EcoRI and XhoI sites. After transformation into yeast together with a LexA-Rev expressing plasmid, lacZ expression was scored on X-Gal containing plates. The results of FIG. 2g show that the minimal portion of hRIP required for interaction with Rev is from residues 426–513, which is within the nucleoporin homology region.

Intracellular Distribution of hRIP in Human and Yeast Cells

Cytoplasmic extract (S100) and nuclear extract were prepared as described (Dignam et al., (1983) Nucl. Acids Res. 11:1475–1489). The nuclear pellet was incubated with 7M urea for 30 minutes at 4° C. and after centrifugation yielded the nuclear pellet extract. 30 μg of each fraction was separated by 10% SDS-PAGE and then immunoblotted with the α-hRIP antibody. FIG. 3a shows that virtually all HeLa hRIP is present in the nuclear extract of fractionated HeLa cells.

Figure 3B:
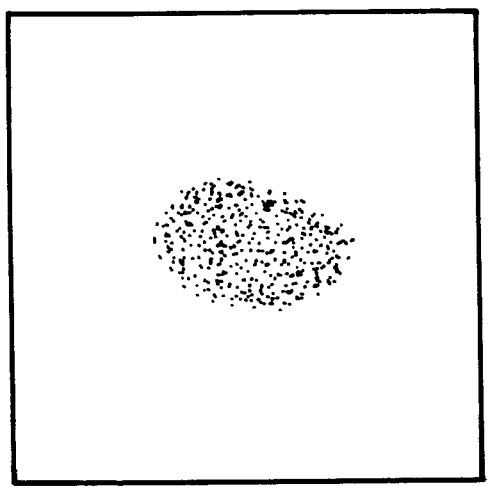
FIG. 3b shows indirect immunofluorescence of HeLa cells with α-hRIP and Mab322 antibody. Mab322 is a monoclonal antibody that recognizes the nucleoporin nup153. The photograph on the bottom left is focused on the nuclear rim; that on the bottom right, on the nuclear surface. The punctate stain at the nuclear periphery is indicated by arrows.
Figure 3B:
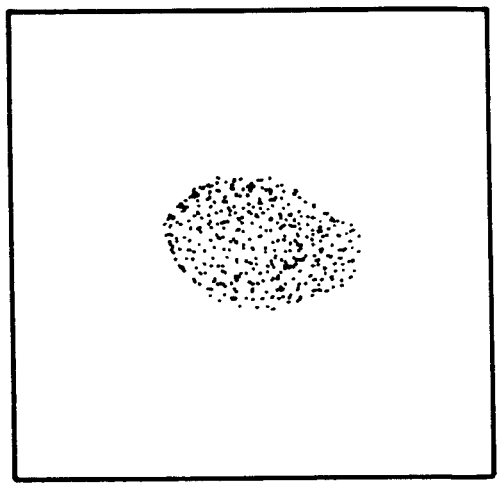
Figure 3B:
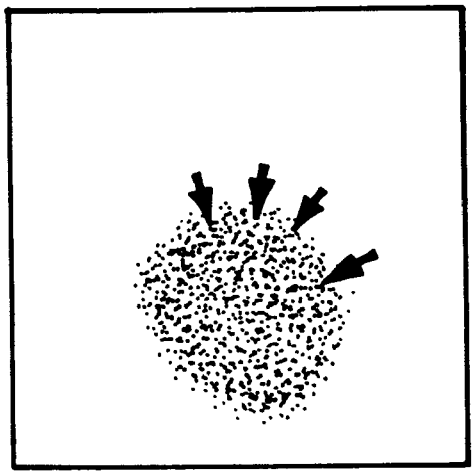
Figure 3B:
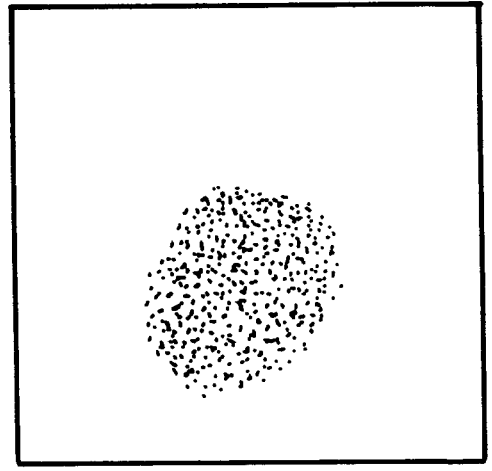

HeLa cells were fixed for immunofluorescence as described (Zhang et al., (1994) Nature 372:809–812) and probed with α-hRIP antibody at 7 μg/ml or Mab322 at a dilution of 1/750. Primary antibodies were then visualized with FITC-labelled goat α rabbit (TAGO, 1:300) or cγ3 labelled sheep α mouse (Sigma, 1:500) secondary antibodies. In FIG. 3b, it can be seen that hRIP is primarily in the nucleoplasm but without the nucleolar exclusion typical of nucleoplasmic proteins. Significantly, focusing on the nuclear rim (bottom left) or the nuclear surface (bottom right) revealed a punctate staining pattern resembling that of nucleoporins. However, unlike the typical nucleoporin pattern, most of the hRIP staining is nucleoplasmic (compare top left and right).

Figure 3C:
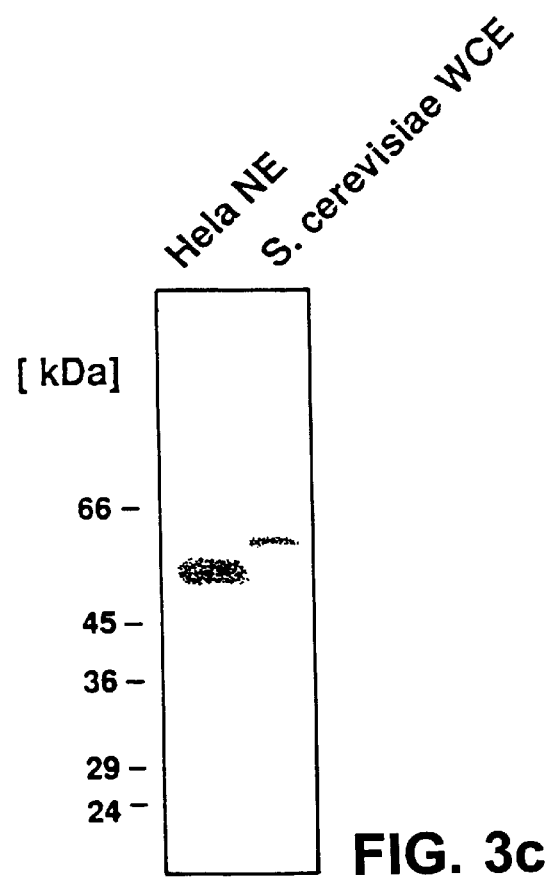
FIG. 3c shows an immunoblot analysis of human (HeLa) and yeast (S. cerevisiae) cells. NE, nuclear extract; WCE, whole-cell extract. Fractions were separated on 10% SDS PAGE and immunoblotted with the α-hRIP antibody. The migration of the molecular mass markers is indicated on the left.
Figure 3D:
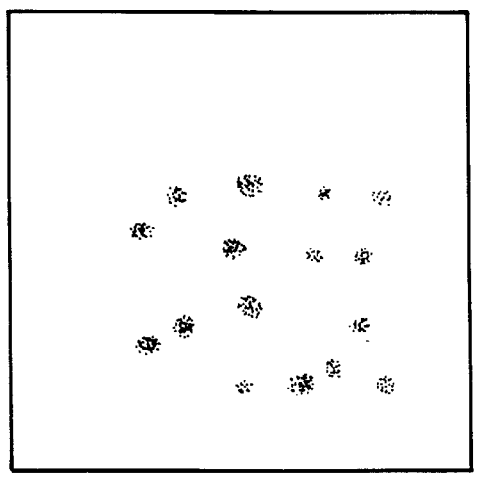
FIG. 3d shows indirect immunofluorescence of yeast cells. Yeast nuclei were made visible by staining of the DNA with the dye Hoechst 33258 (left) and compared to staining with α-hRIP (right).
Figure 3D:
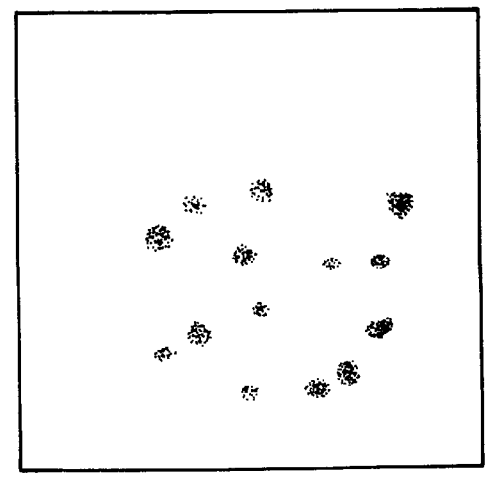

For comparison of yeast whole cell and HeLa nuclear extracts, 70 μg of each fraction was separated on 10% SDS PACE and immunoblotted with the α-hRIP antibody. Yeast cells were also fixed for immunofluorescence and probed with the α-hRIP antibody. The antibody detected a single 63 kDa yeast polypeptide (FIG. 3c), very close in size to hRIP (59 kDa). The indirect immunofluorescence experiment of FIG. 3d shows that the yeast polypeptide, like HeLa hRIP, is nuclear-localized. These results strongly suggest that S. cerevisiae contains an hRIP homologue.

Rev Assay in CV-1 Cells

Figure 4:
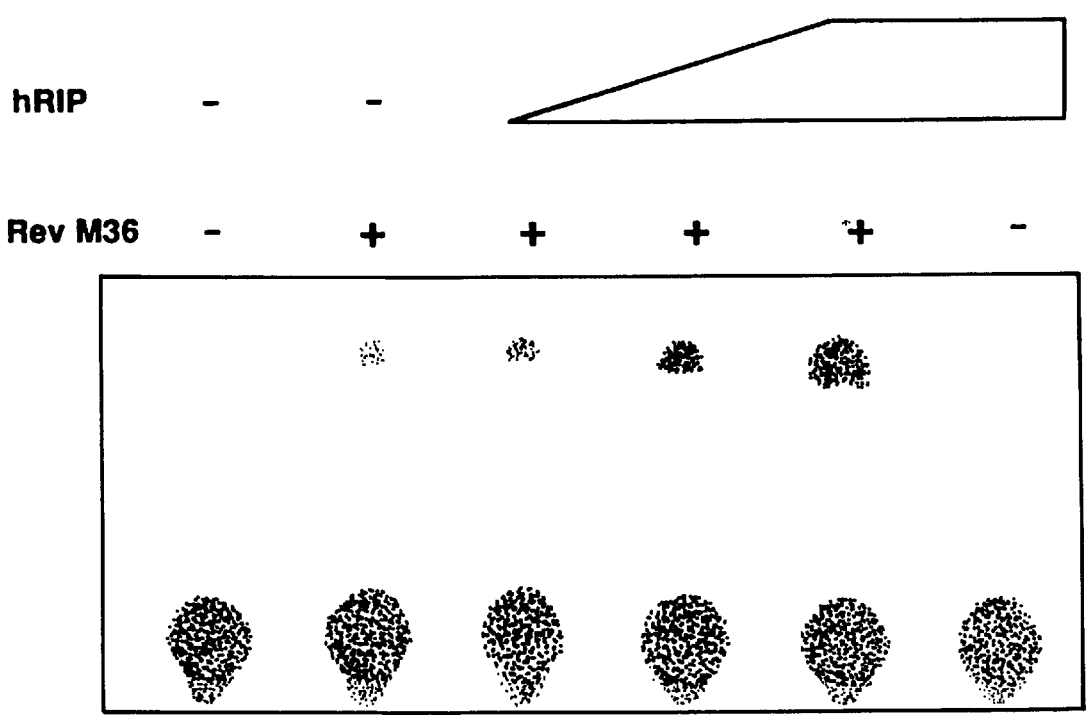
FIG. 4 shows the effect of over-expression of hRIP on the activity of a Rev activation domain mutant. CAT activity was assayed following cotransfection of reporter plasmid pCM128 and the Rev expression plasmid pcRevM36 into CV-1 cells in the absence (−) or the presence (+) of increasing amounts (1, 2.5, 5 μg.) of an hRIP expression vector.

A Rev effector domain mutant is presumably inactive due to a decreased affinity for its cellular cofactor. Overexpression of a potential Rev target molecule may restore some activity upon such a partially defective mutant: by mass action, the elevated concentration should increase interaction between the Rev mutant and its target. FIG. 4 shows such an experiment with the Rev mutant M36, which retains 15% Rev function. Rev activity was measured in a cotransfection assay using a CAT reporter plasmid (pCM128), which has a single intron containing both the RRE and the bacterial CAT coding sequence. The hRIP expression vector was derived by cloning the full-length hRIP cDNA into pcDNAI (Invitrogen). Transfection was by the calcium phosphate procedure and in each case the total amount of pcDNAI derivative was maintained at 5 μg. 0.5 μg of the CAT reporter plasmid pCM128 was cotransfected with 0.5 μg of the Rev expression plasmid pcRevM36 (Malim et al., (1991) *J. Virol.* 65:4248–4254) into CV-1 cells in the absence(–) or presence of increasing amounts (1, 2.5, 5 μg) of an hRIP expression vector.

FIG. 4 shows that co-expression of hRIP resulted in a dose-dependent increase in Rev-M36 activity (FIG. 4, lanes 2–5). In the absence of Rev, hRIP did not affect expression of pCM128 (FIG. 4, lane 6). Comparable overexpression of hRIP did not increase expression of cotransfected RSV- and CMV-driven reporter genes. Taken together, these data strongly suggest that the interaction between Rev and hRIP is functionally relevant.

The experiments of this Example indicate that hRIP has properties expected of a Rev cellular cofactor. First, hRIP contains sequence motifs characteristic of nucleoporins, a class of proteins that mediate nucleocytoplasmic trafficking (FIG. 2). Second, the interaction between hRIP and Rev precisely correlates with the activity of Rev effector domain mutants (FIG. 1). Third, the intracellular distribution of hRIP is that expected of a Rev cofactor (FIGS. 3 a, b). Fourth, an apparent hRIP homologue is present in a variety of cell types, including *S. cereviseae*, that support a Rev response (FIGS. 3 c, d). Finally, overexpression of hRIP can increase the activity of a Rev effector domain mutant (FIG. 4). Proposed models for Rev action include a direct enhancement of viral RNA nuclear export, or alternatively an inhibition of pre-mRNA splicing. An important basis for distinguishing between these models is the function of the cellular factor with which Rev interacts. The sequence features and cellular distribution of hRIP strongly suggest a direct role in nucleocytoplasmic trafficking.

Example 2
High-throughput Screening of Anti-hRIP Compounds

Corning ELISA strip wells (8 wells per strip) are coated with avidin (1.0 ug per well) by incubating avidin (200 ul of a 5 ug/ml stock) in coupling buffer (per liter: 1.6 g $Na_2CO_3$, 2.9 g NaHCO, 0.9 g $NaN_3$) in the well for 12 hours at 4° C. The buffer is decanted, and nonspecific binding sites on the wells are blocked with 1% skim milk in phosphate-buffered saline (PBS) for 1 hour at 37° C. Blocking buffer is discarded, and a RRE-containing RNA oligonucleotide (1 pmol/well) is added to the wells and incubated for 30 min at room temperature. The oligonucleotide is single-stranded and contains a biotin tag on the end of one strand.

The oligonucleotide-containing solution is then removed, and the wells are washed with 1% milk in PBS. HIV Rev is mixed with partially purified hRIP that had been metabolically labelled with $^{35}$S-methionine, all in HEG buffer (0.1M KCl, 25 mM HEPES pH 7.9, 0.5 mM EDTA, 20% glycerol, 0.01% LDAO, 0.1M AEBSF, 0.1M Na metabisulfite, 10 mM β-mercaptoethanol) plus 200 ug/ml bovine serum albumin (BSA).

The protein mixture is then added to the prepared wells and incubated for 30 minutes at room temperature. Samples are then removed, and the wells are washed three times with the PBS/milk solution. Wells are separated and put into scintillation vials, scintillation cocktail is added, and samples are counted in a liquid scintillation counter.

Binding of hRIP to the wells is found to be dependent on the presence of Rev, bound in turn to the RRE-containing oligonucleotide. Small molecules, whether purified or present in natural or synthetic mixtures, are introduced into the assay at concentrations ranging from about 20 to about 200 μM, and appropriate solvent controls are also performed. Compounds that inhibit binding of hRIP by more than about 30% are identified, and the inhibitory activity purified if not already available in pure form.

Compounds identified as described above are then tested for their ability to inhibit Rev-dependent gene expression in a mammalian tissue culture system.

Example 3
Alternate High-throughput Screening of anti-hRIP Compounds

A protein A (pA)-hRIP fusion protein is generated by inserting the coding sequence of hRIP in frame downstream of the pA coding sequence of the plasmid pRIT2T (Pharmacia Biotech). The fusion protein is induced, extracted and purified according to the manufacturer's recommended conditions. This procedure can also be carried out for the preparation of a pA-HIV Rev fusion protein except that the downstream coding sequence is that of HIV Rev protein; all other steps would remain the same.

A Dynatech Microlite 2 microtiter plate or equivalent high protein-binding capacity plate, is coated with 1 μg/well human IgG by incubating 300 μl 3.33 μg/ml human IgG (Sigma) in coating buffer (0.2M sodium carbonate, pH 9.4) in the well for 4–12 hours at 4° C. The coating buffer is then decanted and the wells are washed five times with 300 μl PBS. 300 μl blocking buffer (SuperBlock™ blocking buffer; Pierce) containing 3.33 μg/ml pA-hRIP or pA-HIV Rev are added and the plate is incubated for 4 or more hours at 4 degrees celsius. The plates may be stored in this form at 4° C. until ready for use. When ready for use the plates are washed five times with 300 μl PBS. Test compound at a final concentration of 20–200 μM and labeled HIV Rev or hRIP, whichever is not added during the coating step, are suspended in HEG buffer containing 200 μg/ml BSA in a final total volume of 150 μl and are added and the reaction is incubated at room temperature with gentle agitation for 60 minutes. The plate is then washed five times with PBS using a Dynatech plate washer or equivalent. Bound labeled protein is quantitated by adding 250 μl Microscint (Packard) per well and is counted in a Wallac Microbeta liquid scintillation counter.

As an alternative, the protein A fusion protein and the second, non-fusion protein can be incubated in the presence of test compound in polypropylene microtiter plates under the same buffer and incubation conditions described above. The reaction mix is then transferred to the wells of a microtiter plate coated with human IgG (which is prepared as described above, and is stored in blocking buffer and is washed five times with 300 μl PBS immediately before use) and is incubated for 60 minutes at room temperature with gentle agitation. Retention of radioactive protein is quantitated as above.

Interaction of HIV Rev and hRIP, which is measured as retention of radioactivity on the plate, is dependent on human IgG coating the plate and wild-type HIV Rev and hRIP, one of which must be fused to pA. Compounds or extracts that inhibit retention of radioactivity by more than 30% are identified and the inhibitory activity is further purified if necessary. Inhibitory compounds are further tested for their ability to inhibit Rev-dependent gene expression and HIV replication in a mammalian tissue culture system.

Other fusion or modified protein systems that are contemplated include, but are not limited to, glutathione-S-transferase, maltose binding protein, influenza virus hemagglutinin, FLAG™ and hexahistidine fusions to HIV Rev or hRIP which are prepared, expressed, and purified by published methods or biotinylated HIV Rev or hRIP which are prepared using reactive biotin precursors available commercially. The purified fusion or modified protein is immobilized on a microtiter plate containing the appropriate ligand for each fusion protein (e.g. glutathione, amylose, CA157 antibody, etc., respectively) and the assay is carried out and the results evaluated in essentially the same manner as described above.

Example 4
Treatment of Viral Infections

A compound is identified by the methods described in Example 2 as possessing anti-hRIP activity is titrated for its viral replication-inhibiting properties. That is, the concentration range in which the compound effectively suppresses the replication of HIV is measured using methods that are standard in the art. The toxicity of the compound for mammalian cells over the identical concentration range is then tested using standard procedures.

A pharmaceutical formulation is prepared containing the above compound in a concentration effective to prevent replication of HIV without affecting the viability or function of mammalian cells, i.e., at a concentration at which the compound exhibits minimal or no toxicity, or toxicity at a level generally accepted in the art. The above formulation is administered using an oral, transdermal, intranasal, rectal, intravenous, intramuscular, or subcutaneous route to treat HIV infection in a human.

OTHER EMBODIMENTS

While the invention has been described in conjunction with the detailed description, the foregoing description is intended to illustrate and not limit the scope of the invention, which is defined by the scope of the appended claims. Other aspects, advantages, and modifications are within the scope of the following claims.

What is claimed is:

1. An isolated human Rev interacting polypeptide (hRIP) encoded by a nucleic acid molecule that (1) hybridizes to the complement of the cDNA of SEQ ID NO:2 under stringent conditions of 0.1×SSC and 65° C., (2) has the nucleic acid sequence of SEQ ID NO:2, or (3) is a variant of SEQ ID NO:2 based on the degeneracy of the genetic code.

2. An isolated complex consisting essentially of (1) a human Rev interacting polypeptide (hRIP) of claim 1, and (2) a factor that binds to the hRIP.

3. The complex of claim 2, wherein the factor is selected from the group consisting of an HIV Rev polypeptide, an HIV Rev-RRE complex, and an HTLV Rex polypeptide.

4. A method for producing a human Rev interacting polypeptide (hRIP), the method comprising:
    culturing a cell containing a nucleic acid molecule encoding the hRIP of claim 1; and
    isolating the polypeptide from the cell.

5. An isolated hRIP polypeptide, the polypeptide comprising an amino acid sequence identical to a sequence of about 15 to 50 consecutive amino acids within the hRIP of claim 1.

6. The isolated hRIP of claim 1, wherein the hRIP is modified by phosphorylation, dephosphorylation, glycosylation, or deglycosylation.

7. The isolated hRIP of claim 1, wherein the hRIP is modified by the addition of a label.

8. An isolated human Rev interacting polypeptide (hRIP) having the amino acid sequence of SEQ ID NO:1.

9. An isolated hRIP polypeptide, the polypeptide comprising an amino acid sequence identical to a sequence of about 15 to 50 consecutive amino acids within the hRIP of claim 8.

10. The isolated hRIP of claim 8, wherein the hRIP is modified by phosphorylation, dephosphorylation, glycosylation, or deglycosylation.

11. The isolated hRIP of claim 8, wherein the hRIP is modified by the addition of a label.

12. An isolated complex consisting essentially of (1) an hRIP of claim 8, and (2) a factor that binds to the hRIP.

13. The complex of claim 12, wherein the factor is selected from the group consisting of an HIV Rev polypeptide, an HIV Rev-RRE complex, and an HTLV Rex polypeptide.

14. A method for producing a human Rev interacting polypeptide (hRIP), the method comprising:

culturing a cell containing a nucleic acid molecule encoding the hRIP of claim 8; and isolating the polypeptide from the cell.

* * * * *